United States Patent [19]

Ichijima et al.

[11] Patent Number: 4,814,261
[45] Date of Patent: Mar. 21, 1989

[54] SILVER HALIDE PHOTOGRAPHIC MATERIAL CONTAINING A DEVELOPMENT RESTRAINER OR A PRECURSOR THEREOF

[75] Inventors: Seiji Ichijima; Shigeo Hirano, both of Kanagawa, Japan

[73] Assignee: Fuji Photo Film Co., Ltd., Kanagawa, Japan

[21] Appl. No.: 74,396

[22] Filed: Jul. 16, 1987

[30] Foreign Application Priority Data

Jul. 16, 1986 [JP] Japan .................. 61-167644

[51] Int. Cl.$^4$ .......................... G03C 1/46; G03C 1/08; G03C 7/26; G03C 7/32
[52] U.S. Cl. .................... 430/544; 430/505; 430/552; 430/553; 430/558; 430/956; 430/957; 430/966
[58] Field of Search ............ 430/544, 505, 957, 956, 430/552, 553, 558, 966

[56] References Cited

U.S. PATENT DOCUMENTS

| | | | |
|---|---|---|---|
| 3,961,963 | 6/1976 | Shiba et al. | 430/495 |
| 3,975,395 | 8/1976 | Ohi et al. | 548/251 |
| 3,984,245 | 10/1976 | Hirose et al. | 430/505 |
| 4,015,988 | 4/1977 | Shiba et al. | 430/505 |
| 4,105,452 | 8/1978 | Shiba et al. | 430/386 |
| 4,108,663 | 8/1978 | Tanaka et al. | 430/505 |
| 4,252,893 | 2/1981 | Iwamuro et al. | 430/551 |
| 4,268,621 | 5/1981 | Ogi et al. | 430/551 |
| 4,332,878 | 6/1982 | Akimura et al. | 430/434 |
| 4,345,024 | 8/1982 | Hirano et al. | 430/505 |
| 4,377,634 | 3/1983 | Mifune et al. | 430/440 |
| 4,387,159 | 6/1983 | Engelmann et al. | 430/544 |
| 4,476,219 | 10/1984 | Sakanoue et al. | 430/553 |
| 4,636,456 | 1/1987 | Takamashi et al. | 430/489 |

FOREIGN PATENT DOCUMENTS

2036355 6/1980 United Kingdom .

*Primary Examiner*—Mukund J. Shah
*Attorney, Agent, or Firm*—Sughrue, Mion, Zinn, Macpeak & Seas

[57] ABSTRACT

A silver halide photographic material is disclosed. The photographic material comprises a support having provided thereon at least one light-sensitive silver halide emulsion layer, the silver halide emulsion layer or a layer adjacent to the emulsion layer comprising a compound represented by the following formula (I):

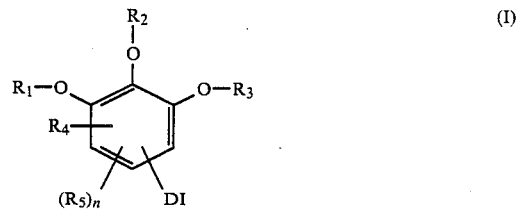

wherein $R_1$, $R_2$, and $R_3$, which may be the same or different, each represents a hydrogen atom or a group cleaved by an alkali; $R_4$ represents an electron attracting group having $\sigma p$ value of Hammett's substituent constant of 0.3 or more; $R_5$ represents a group substitutable on the benzene ring; n represents 0 or 1; and DI represents a development restrainer or a precursor thereof; and when any two of $R_1$, $R_2$, $R_3$, $R_4$ and $R_5$ are adjacent each other, each of the two groups may represent a divalent group and the two groups may be bonded to form a heterocyclic group.

25 Claims, No Drawings

SILVER HALIDE PHOTOGRAPHIC MATERIAL CONTAINING A DEVELOPMENT RESTRAINER OR A PRECURSOR THEREOF

FIELD OF THE INVENTION

The present invention relates to a silver halide photographic material having good image quality. More particularly, the present invention relates to a silver halide photographic material comprising a compound which is oxidized and cleaves a development restrainer during development processing.

BACKGROUND OF THE INVENTION

Compounds which release a photographically useful group through oxidation and reduction reaction are known.

For example, hydroquinone derivatives which release a development restrainer are disclosed in U.S. Pat. Nos. 3,379,529, 3,620,746, 4,144,071, 4,377,634, 4,332,878, 3,930,863 and the like. Furthermore, catechol derivatives which release a development restrainer are disclosed in British Pat. No. 1,400,149.

As described in the above-described patents, conventional compounds have been used for various purposes depending upon the type of light-sensitive material. Among those compounds, hydroquinones which release a development restrainer are effective for the purpose of improving sharpness, graininess, and color reproduction in color photographic light-sensitive material. However, with the recent demand for improved photographic properties, conventional compounds are no longer satisfactory.

Furthermore, there has been a need for a compound which improves dot quality in silver halide photographic material which undergoes a photomechanical process.

Still further, there is a need for a material to improve sharpness in black-and-white photographic light-sensitive material used for X-ray photography.

The above-described conventional and well known compounds fall short of the above-described objectives because they are readily oxidized and immediately release a development restrainer upon development. Those compounds are extremely unstable and are oxidized by air during storage of the light-sensitive materials in which they have been incorporated.

U.S. Pat. No. 4,476,219 discloses gallic acid amides which improve graininess to some extent, but are not satisfactory and additional improvement is necessary.

SUMMARY OF THE INVENTION

An objective of the present invention is to provide a photographic material having good storage stability, graininess, and sharpness.

The above objective can be attained by a silver halide photographic material comprising a support having provided thereon at least one light-sensitive silver halide emulsion layer, the silver halide emulsion layer or a layer adjacent to the emulsion layer comprising a compound represented by the following formula (I):

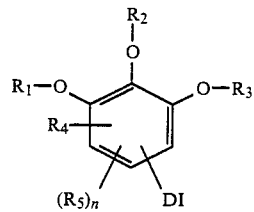

wherein $R_1$, $R_2$ and $R_3$, which may be the same or different, each represents a hydrogen atom or a group cleaved by an alkali; $R_4$ represents an electron attracting group having $\sigma p$ value of Hammett's substituent constant of 0.3 or more; $R_5$ represents a group substitutable on the benzene ring; n represents 0 or 1; and DI represents a development restrainer or a precursor thereof; and when any two of $R_1$, $R_2$, $R_3$, $R_4$, and $R_5$ are adjacent each other, each of the two groups may represent a divalent group and the two groups may be bonded to form a heterocyclic group.

DETAILED DESCRIPTION OF THE INVENTION

The compounds represented by the formula (I) are hereinafter described in more detail. In the following explanation, $R_6$, $R_7$ and $R_8$ are an aliphatic group, an aromatic group or a heterocyclic group, $R_9$ and $R_{10}$ are a hydrogen atom, an aliphatic group, an aromatic group or a heterocyclic group.

$R_1$, $R_2$ and $R_3$ are preferably a hydrogen atom, and when $R_1$, $R_2$ and $R_3$ are a group cleaved by an alkali, typical examples thereof are an $R_6$—CO— group, an $R_6$OCO— group, an NC—$CH_2CH_2$— group, or an $R_6$—$SO_2CH_2CH_2$— group wherein $R_6$ is an aliphatic group, an aromatic group or a heterocyclic group.

When $R_1$ and $R_2$ (or $R_2$ and $R_3$) combine to form a ring structure, preferred examples are as follows:

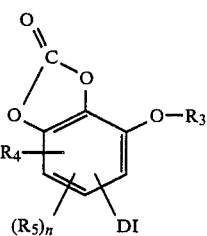

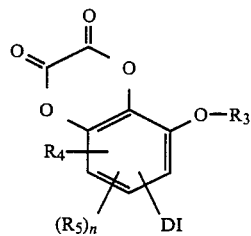

In the above formulae, $R_3$, $R_4$, $R_5$, DI and n are defined as in formula (I) above.

In a more preferred embodiment, $R_4$ is an $R_9$OOC— group, an

group, an $R_7SO_2$— group, an

group, an $R_9CO$— group or a cyano group, wherein $R_9$ and $R_{10}$ may be a hydrogen atom, an aliphatic group, an aromatic group or a heterocyclic group.

n is preferably 0, and when n is 1, $R_5$ is a halogen atom, an $R_8S$— group, or a group as defined for $R_8$, wherein $R_8$ may be an aliphatic group, an aromatic group, or a heterocyclic group.

When $R_6$, $R_7$, $R_8$, $R_9$ or $R_{10}$ is an aliphatic group, they each may be saturated or unsaturated, chain-like or ring-like, linear or branched, substituted or unsubstituted, having from 1 to 40 carbon atoms and preferably from 1 to 18 carbon atoms. Typical examples thereof are a methyl group, an ethyl group, a propyl group, a butyl group, a t-butyl group, a hexyl group, a cyclohexyl group, an octyl group, a 2-ethylhexyl group, a dodecyl group, a tetradecyl group, a hexadecyl group, an octadecyl group or a 2-hexyldecyl group.

When $R_6$, $R_7$, $R_8$, $R_9$ or $R_{10}$ is an aromatic group, the aromatic group is preferably a substituted or unsubstituted phenyl group or a substituted or unsubstituted naphthyl group having from 6 to 20 carbon atoms.

When $R_6$, $R_7$, $R_8$, $R_9$ or $R_{10}$ is a heterocyclic group, hetero atoms include one or more nitrogen atoms, one or more oxygen atoms, or one or more sulfur atoms, and a 3- to 8-membered ring heterocyclic group having from 1 to 7 carbon atoms is preferred. Typical examples of the heterocyclic group are a 2-pyridyl group, a 1,2,4-triazol-3-yl group, a thiadiazolyl group or a furyl group.

When the above-described aliphatic group, aromatic group and heterocyclic group have a substituent, typical examples of the substituent are a halogen atom, an aromatic group, an aliphatic oxycarbonyl group, a carbonamide group, a sulfonamide group, a carbamoyl group, an aromatic oxy group, an aliphatic oxy group, an imide group, a nitro group, an aliphatic thio group, a hydroxyl group, an aromatic oxycarbonyl group, an amino group, an aliphatic group, a heterocyclic ring or a cyano group. The number of carbon atoms contained in these substituents is from 0 to 30.

When DI is a development restrainer in the formula (I), DI is a tetrazolylthio group, a thiazolylthio group, a benzothiazolylthio group, a benzoxazolylthio group, a benzotriazolyl group; an indazolyl group, a benzimidazolylthio group, a triazolylthio group, a thiadiazolylthio group, a thioether substituted triazolyl group (for example, a development restrainer as disclosed in U.S. Pat. No. 4,579,816) or an oxadiazolylthio group.

These development restrainers can have the same substituents as the above-described aromatic groups and heterocyclic groups have at the positions to be substituted. The total number of carbon atoms contained in the substituents is preferably 15 or less.

The development restrainer exhibits a development restraining property after being released and a portion thereof goes into a color developing solution. The development restrainer may be decomposed or changed to a compound which does not have an effect upon photographic development. Examples of such development restrainers are disclosed, for example, in U.S. Pat. No. 4,477,563, Japanese Patent Application (OPI) Nos. 218644/85, 221750/85, 233650/85 and 11743/86 (the term "OPI" as used herein refers to a "published unexamined Japanese patent application").

The group represented by DI in formula (I) may be a precursor of a development restrainer, but is preferably a development restrainer. Examples of development restrainer precursors are as follows:

*—TIME—DI' (II)

wherein the mark * represents the position at which a group except DI is bonded in formula (I) and TIME represents a group which cleaves DI' after being cleaved as TIME—DI' and DI' has the same meaning as that of DI when DI represents a development restrainer.

As the groups represented by TIME, there are, for example, the following linkage groups:

(1) Groups utilizing the cleavage reaction of a hemiacetal:

Examples of these groups are the groups shown by formula (T-1) described in U.S. Pat. No. 4,146,396 and 4,652,516 and Japanese Patent Application (OPI) No. 249148/85 (corresponding to U.S. patent application Ser. No. 737,853).

wherein the mark * represents a position bonding the left side of the group in formula (II); the mark ** represents a position bonding the right side of the group in formula (II); W represents an oxygen atom, a sulfur atom, or

(wherein $R_{23}$ represents an organic substituent); $R_{21}$ and $R_{22}$ each represents a hydrogen atom or a substituent; and t represents 1 or 2; when t is 2, the two $R_{21}$s and $R_{22}$s each may be the same or different and the group shown by formula (T-1) includes the case wherein two of the $R_{21}$, $R_{22}$ and $R_{23}$ combine with each other to form a cyclic structure.

Specific examples of the group shown by formula (T-1) described above are illustrated below:

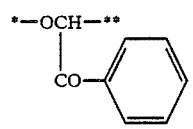

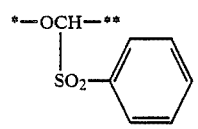

-continued

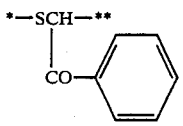
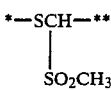
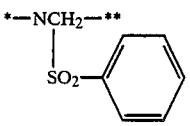
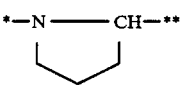
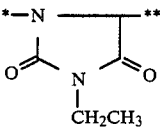
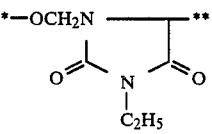
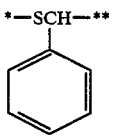
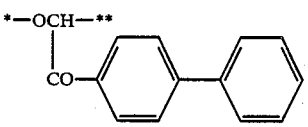
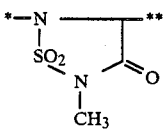
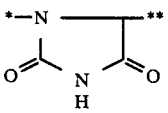
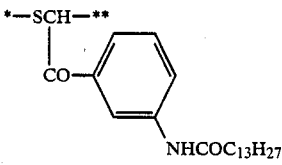

(2) Groups causing a cleavage reaction by utilizing an intramolecular nucleophilic reaction:

Examples of the groups are the timing groups described in U.S. Pat. No. 4,248,962 and are represented by formula (T-2):

$$*-Nu-Link-E-** \qquad (T-2)$$

wherein the mark * represents a position bonding the left side of the group in formula (II); the mark  represents a position bonding the right side of the group in formula (II); Nu represents a nucleophilic group such as an oxygen atom and a sulfur atom; E represents an electrophilic group which can cleave the linkage to  by the nucleophilic attack from Nu; and Link represents a linkage group sterically connecting Nu and E so that they can cause an intramolecular nucleophilic reaction.

Specific examples of the groups shown by formula (T-2) are illustrated below.

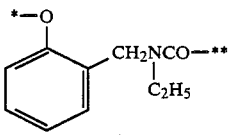
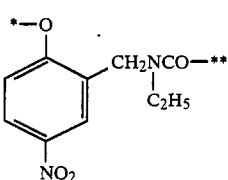
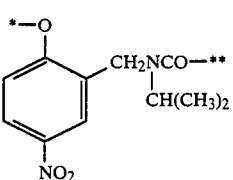
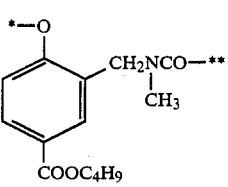
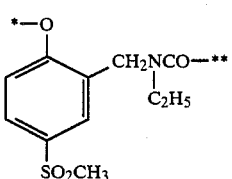
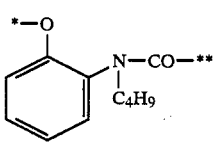
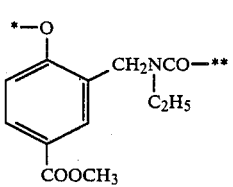

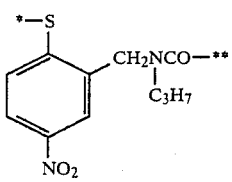
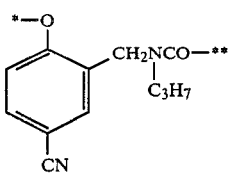
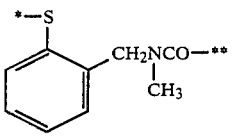
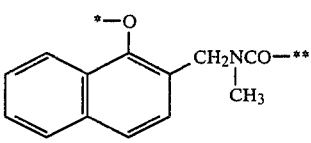
(3) Groups causing a cleavage reaction by utilizing an electron transfer reaction along the conjugated system:
Examples of the groups are described in U.S. Pat. Nos. 4,409,323 and 4,421,845 and are represented by formula (T-3):
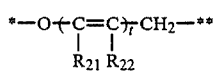
(T-3)
wherein the mark *, the mark **, $R_{21}$, $R_{22}$ and t have the same significance as defined above for formula (T-1).
Specific examples of the groups are illustrated below.
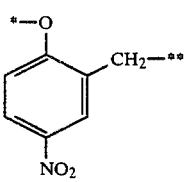
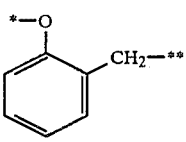
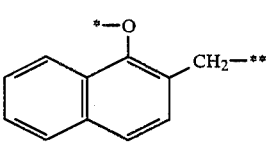
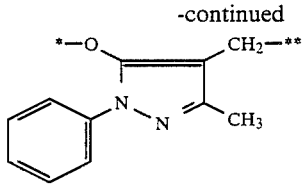
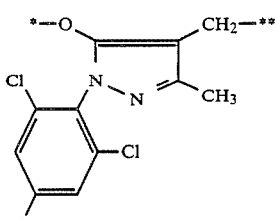
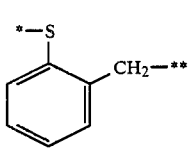
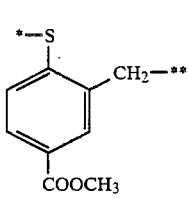
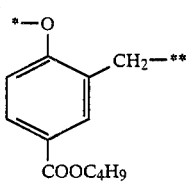
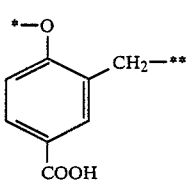
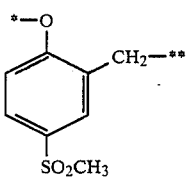
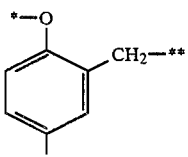
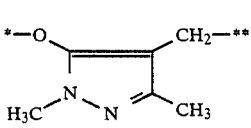

(4) Groups utilizing a cleavage reaction by the hydrolysis of an ester:

Examples of the groups are the linkage groups described in West German Patent Application (OLS) No. 2,626,315 (OLS: Offenlegunsshrift) (corresponding to British Pat. No. 1,531,927), such as those represented by formulae (T-4):

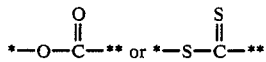
(T-4)

wherein the mark * and the mark ** have the same significance as defined above for formula (T-1).

The compound represented by formula (I) of the present invention is generally used in an amount of $1 \times 10^{-7}$ to $5 \times 10^{-1}$ mol per mol of silver which is present in the same layer as said compound or in a layer which is adjacent to the layer containing said compound.

The effects of the compound of the present invention are described in more detail in (1) to (4) below.

(1) The compounds represented by formula (I) of the present invention are used in multilayer multi-color photographic materials comprising a support having coated thereon multiple layers having at least two different spectral sensitivities for the primary purpose of improving granularity, sharpness, color reproduction and making sensitivities higher. The multilayer multicolor photographic material generally has at least one red-sensitive emulsion layer, at least one green-sensitive emulsion layer, and at least one blue-sensitive emulsion layer, respectively, on a support. The order of these layers can be optionally selected. The compound of the present invention can be used in any layers such as a high sensitive layer, a medium sensitive layer, a low sensitive layer, a light-sensitive silver halide emulsion layer or a layer adjacent to a red-, green- or blue-sensitive emulsion layer.

The amount of the compound of the present invention which is incorporated into the photographic material depends upon the structure of the compound and the end use thereof, and is preferably from $1 \times 10^{-7}$ to 0.5 mol, more preferably from $1 \times 10^{-6}$ to $1 \times 10^{-1}$ mol, per mol of silver which is present in the same layer as said compound or in a layer which is adjacent to the layer containing said compound.

The compounds of the present invention can be used in a layer by itself or can be used with a known coupler. When the compound of the present invention is used together with a color image forming coupler, the ratio of the compound to the other color image forming coupler (the compound of the present invention/the other color image forming coupler) is 0.1/99.9 to 90/10, preferably 1/99 to 50/50, by mol.

(2) The compounds of the present invention improve the quality of a silver halide photographic material for a photomechanical process which has a silver chlorobromide or silver chloroiodobromide emulsion layer (the emulsion is preferably monodispersed) containing at least 60 mol% silver chloride and 0 to 5 mol% silver iodide relative to the total silver halide concentration, and furthermore which has polyalkylene oxides.

One quality that can be improved by using the above formulation is lengthening of dot gradation without deteriorating dot quality. In this case, the compound of the present invention is used preferably in a ratio of from $1 \times 10^{-7}$ mol to $1 \times 10^{-1}$ mol, particularly from $1 \times 10^{-6}$ mol to $1 \times 10^{-2}$ mol, per mol of silver halide.

(3) The compounds of formula (I) of the present invention improve (lenghten) dot gradation of a photographic material having a monodispersed silver halide emulsion layer which is capable of forming a superhigh contrast negative image with a stable developing solution in the presence of hydrazine derivatives, as disclosed in U.S. Pat. Nos. 4,224,401, 4,168,977, 4,241,164, 4,311,781, 4,272,606, 4,221,857, 4,243,739, 4,272,614, 4,269,929 and the like without deteriorating dot quality. In this case, the compound of the present invention is used in a ratio of $1 \times 10^{-5}$ mol to $8 \times 10^{-2}$ mol, preferably from $1 \times 10^{"4}$ mol to $5 \times 10^{-2}$ mol, per mol of silver halide.

(4) The compounds of formula (I) of the present invention improve the sharpness of images formed with black-and-white photographic material, particularly light-sensitive material for X-ray photography having on at least one of the surfaces of the support a silver iodobromide or silver chloroiodobromide emulsion layer containing silver chloride in a ratio of from 0 to 50 mol% and silver iodide in a ratio of not more than 15 mol%. When used for this purpose, the addition amount of the compound is $1 \times 10^{-6}$ to $1 \times 10^{-1}$ mol, preferably from $1 \times 10^{-5}$ to $5 \times 10^{-2}$ mol, per mol of silver halide.

The compounds of formula (I) of the present invention are suitable for photographic light-sensitive materials for various uses such as for recording an electron ray image. They may be used in a black-and-white photographic material with high resolving power, a black-and-white photographic material for diffusion transfer, a color X-ray photographic material or a color photographic material for diffusion transfer.

The specific examples of the present invention are presented below. These examples are intended to be illustrative only and should not be construed as limiting the scope of the present invention described herein.

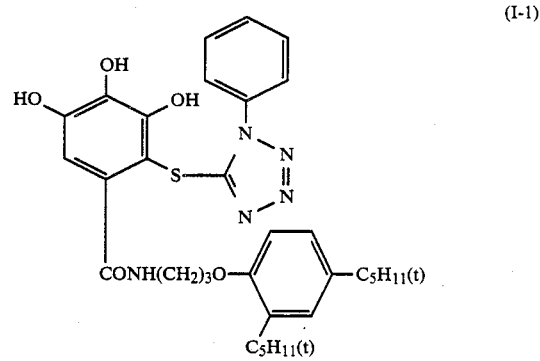
(I-1)

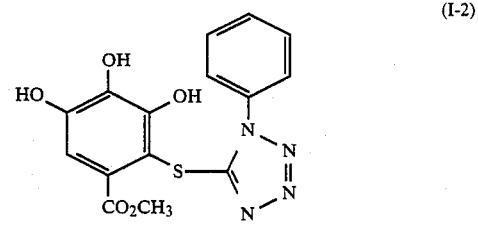
(I-2)

-continued
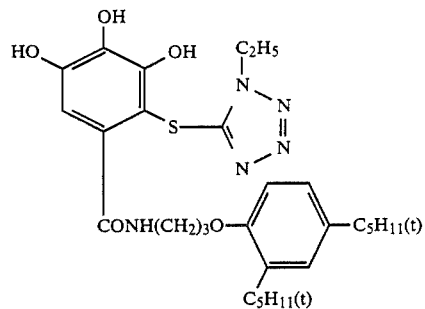
(I-3)
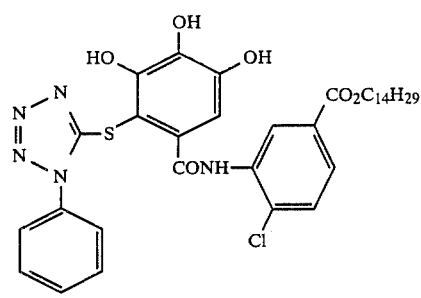
(I-4)
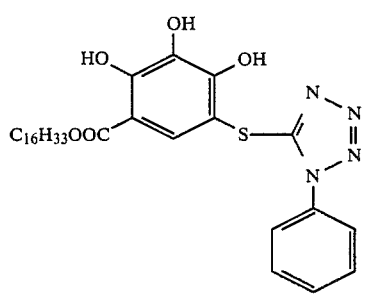
(I-5)
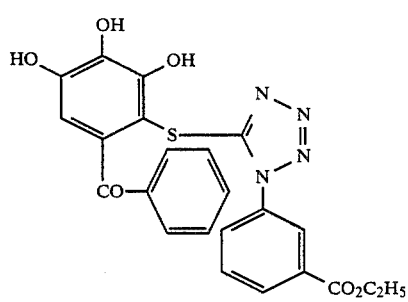
(I-6)
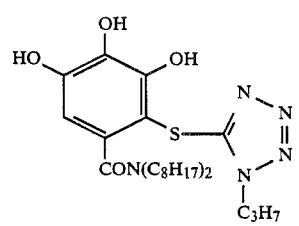
(I-7)
-continued
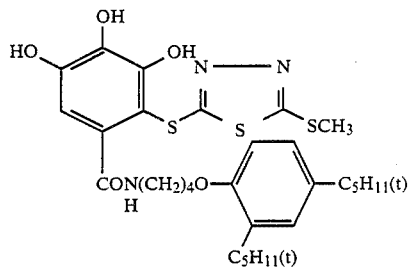
(I-8)
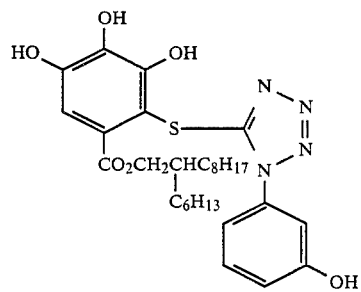
(I-9)
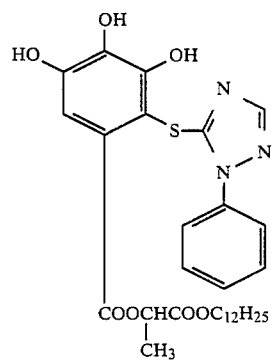
(I-10)
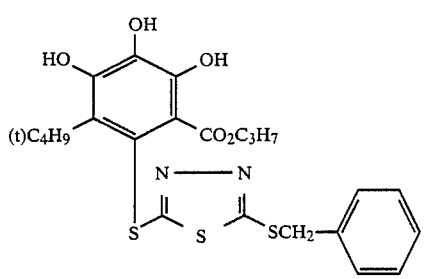
(I-11)
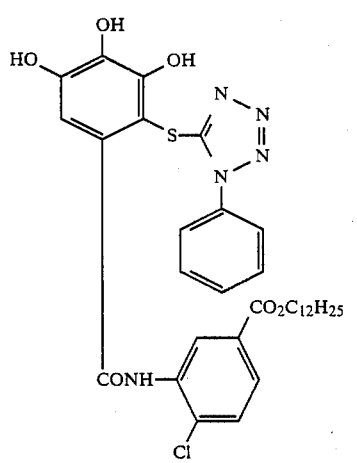
(I-12)

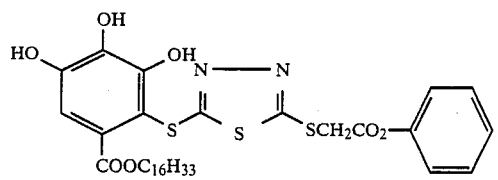 (I-13)
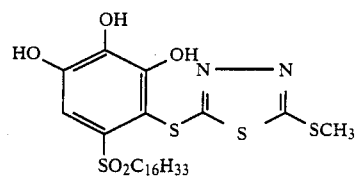 (I-18)
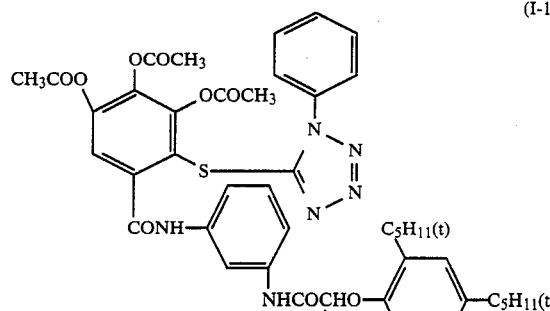 (I-14)
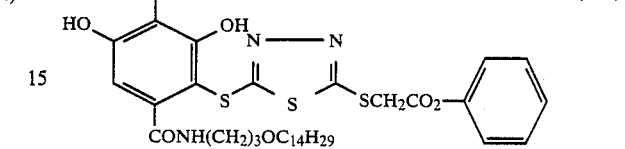 (I-19)
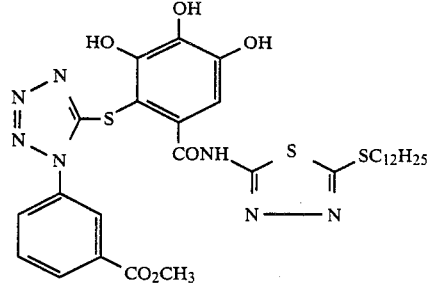 (I-20)
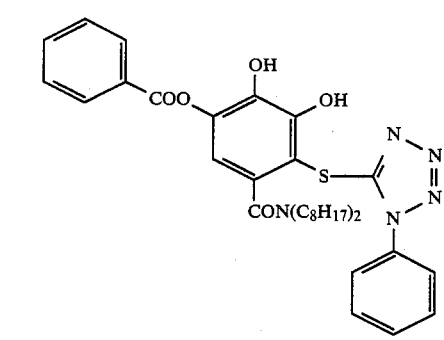 (I-15)
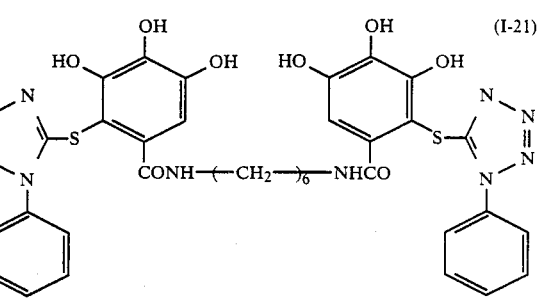 (I-21)
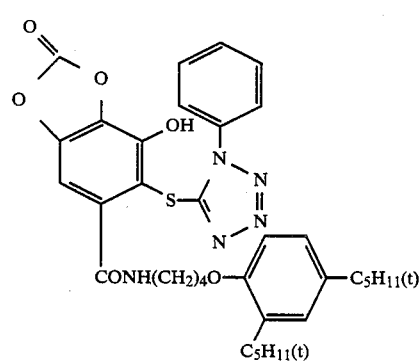 (I-16)
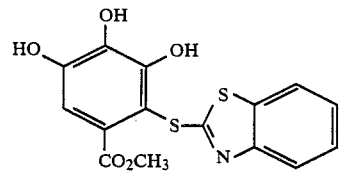 (I-22)
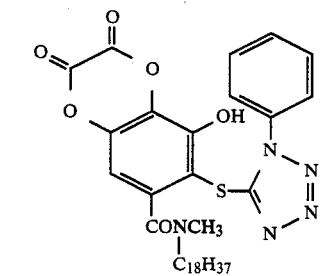 (I-17)
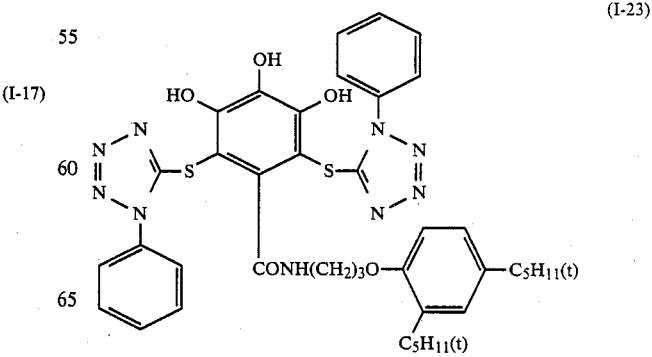 (I-23)

-continued

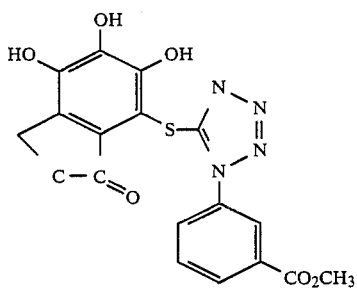 (I-24)

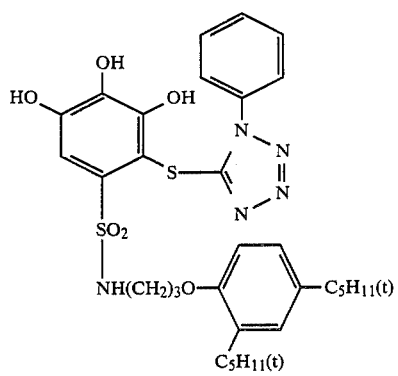 (I-25)

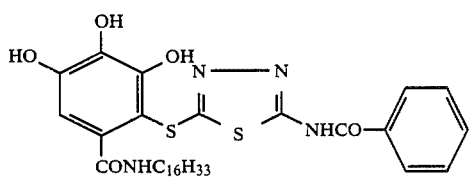 (I-26)

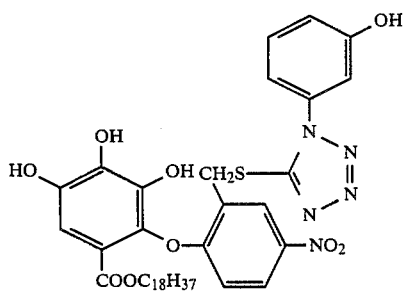 (I-27)

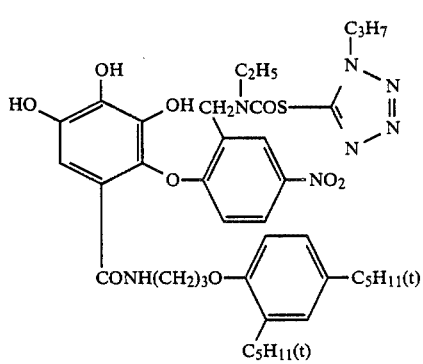 (I-28)

-continued

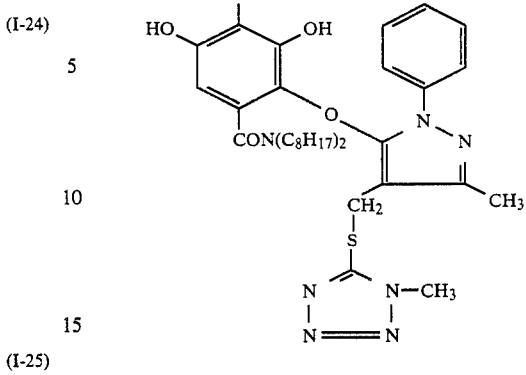 (I-29)

SYNTHESIS EXAMPLE 1

Synthesis of Compound (I-1)

Into 4.5 g of 5-mercapto-1-phenyltetrazole which had been dispersed in 50 ml of chloroform was added 3.4 g of N-chlorosuccinic acid imide while being cooled with ice and the reaction was permitted to proceed for 15 minutes. Into the reaction solution was added 8.9 g of N-[3-(2,4-di-tert-pentylphenoxy)propyl]gallic acid amide (the synthesis method of this compound is disclosed in U.S. Pat. No. 4,476,219) and the reaction was permitted to proceed for 20 minutes while being cooled with ice. After the chloroform vapors were recondensed, 30 ml of acetonitrile was added to crystallize the product. The crystals were filtered and washed with water and again recrystallized with acetonitrile to obtain 6.9 g (55% of theoretical yield) of the intended substance. Melting point was from 175° to 177° C.

SYNTHESIS EXAMPLE 2

Synthesis of Compound (I-2)

Into 17.8 g of 5-mercapto-1-phenyltetrazole which had been dispersed in 100 ml of acetonitrile was added 13.4 g of N-chlorosuccinic acid imide while being cooled with ice and the mixture was stirred for 10 minutes. The reaction was permitted to proceed at room temperature for an additional 30 minutes. Again while being cooled with ice, 18.4 g of methyl gallate was added and the mixture was stirred for 1 hour. The precipitated crystals were filtered and washed with acetonitrile and water and again recrystallized with 180 ml of ethanol to obtain 10.3 g (29% of theoretical yield) of the intended substance. Melting point was from 176° C. to 178° C.

SYNTHESIS EXAMPLE 3

Synthesis of Compound (I-22)

Into the mixed solution of 11.7 g of 2-mercapto-benzothiazole in 70 ml of acetonitrile, 9.4 g of N-chlorosuccinic acid imide was added and was reacted while being cooled with ice for 1 hour. 12.9 g of methyl gallate was added to the reaction solution and the reaction was permitted to proceed further at room temperature for 2 hours. The precipitated crystals were filtered and washed with acetonitrile and subsequently with water and was again recrystallized with the mixed solution of chloroform and a slight amount of ethanol to obtain 10.1 g (41% of theoretical yield) of the intended substance. The melting point was 196° to 198° C.

The couplers which may be used together with the compounds of formula (I) of the present invention are described in detail hereinafter.

The following couplers, for example, are used in the present invention.

Image forming couplers, DIR couplers (couplers as disclosed, for example, in U.S. Pat. Nos. 3,227,554, 4,146,396, 4,248,962, 4,409,323, 4,421,845, 4,477,563 and 3,148,062), slightly diffusible dye forming couplers (couplers as disclosed, for example, in U.S. Pat. Nos. 4,522,915 and 4,420,556), development accelerating- or fogging agent releasing-couplers (couplers as disclosed, for example, in U.S. Pat. No. 4,390,618), colored couplers (couplers as disclosed in U.S. Pat. Nos. 4,004,929, 4,138,258 and 4,070,191), competing couplers (couplers as described, for example, in U.S. Pat. No. 4,130,427), poly-equivalent couplers (couplers as disclosed, for example, in U.S. Pat. Nos. 4,283,472, 4,338,393 and 4,310,618), DIR redox compound releasing couplers (couplers as disclosed, for example, in Japanese patent application (OPI) No. 185950/85), dye releasing couplers which are recolored after coupling-off (e.g., couplers as disclosed in European patent application No. 173,302A2) or various polymeric couplers (couplers as disclosed, for example, in U.S. Pat. Nos. 3,767,412, 3,623,871, 4,367,282, 4,474,870 and the like).

The dyes formed by couplers can be any one of yellow, magenta or cyan. Yellow couplers are, for example, acylacetamide type couplers, and malondiamide type couplers. Magenta couplers are, for example 5-pyrazolone type couplers, pyrazoloimidazole type couplers or pyrazolotriazole type couplers. Cyan couplers are, for example, phenol type couplers or naphthol type couplers. Any couplers can be 4-equivalent couplers or 2-equivalent couplers. Further, couplers which do not substantially form dye can be used. Such couplers are disclosed, for example, in U.S. Pat. Nos. 3,958,993, 3,961,959, 4,315,070, 4,183,752 and 4,171,223.

The couplers preferably used in the present invention are those couplers represented by the following formulae (Cp-1), (Cp-2), (Cp-3), (Cp-4), (Cp-5), (Cp-6), (Cp-7) or (Cp-8).

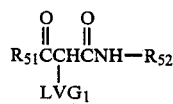
(Cp-1)

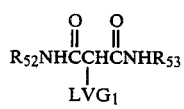
(CP-2)

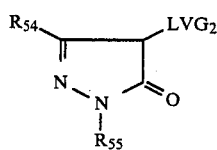
(Cp-3)

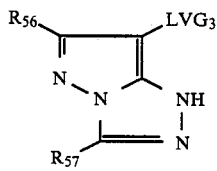
(Cp-4)

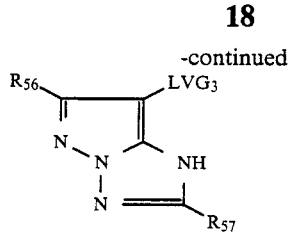
(Cp-5)

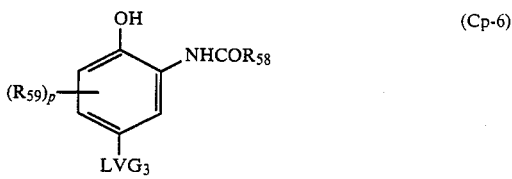
(Cp-6)

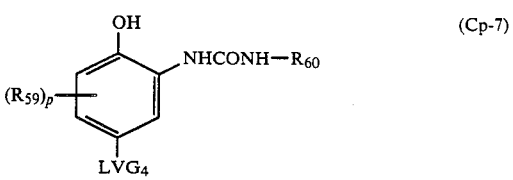
(Cp-7)

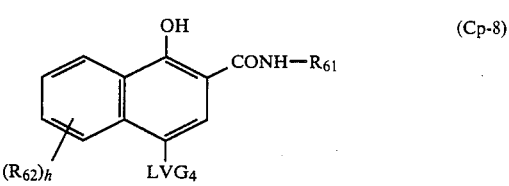
(Cp-8)

$R_{51}$ to $R_{62}$, $LVG_1$ to $LVG_4$, p and h are defined as follows.

In the above formulae, when $R_{51}$ to $R_{62}$ and $LVG_1$ to $LVG_4$ contain nondiffusible groups, they are selected so that the total number of carbon atoms in each formula is from 8 to 40, preferably from 12 to 32, and otherwise the total number of carbon atoms in each formula is preferably 15 or lower. When the couplers are bis type couplers, telomerization type couplers and polymer type couplers, any one of the above-described substituents is a divalent group and bonds the repeating unit. In this instance, the number of carbon atoms can be outside of the above ranges.

In the following descriptions, $R_{41}$ represents an aliphatic group, an aromatic group or a heterocyclic group; $R_{42}$ represents an aromatic group or a heterocyclic group; and $R_{43}$, $R_{44}$ and $R_{45}$ represent a hydrogen atom, an aliphatic group, an aromatic group or a heterocyclic group.

$R_{51}$ has the same definition as that of $R_{41}$. $R_{52}$ and $R_{53}$ have the same definition as that of $R_{42}$. $R_{54}$ represents a group having the same definition as that of $R_{41}$, an

group, an

group, an

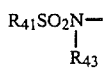

group, an $R_{41}S-$ group, an $R_{43}O-$ group, an

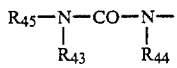

group, an $R_{41}COC-$ group, an

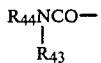

group or an $N\equiv C-$ group. $R_{55}$ represents a group having the same definition as that of $R_{41}$. $R_{56}$ and $R_{57}$ are a group having the same definition as that of $R_{43}$, an $R_{41}S-$ group, an $R_{41}O-$ group, an

group, an

group, an

group, an

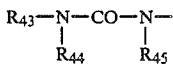

group or an

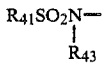

group. $R_{58}$ represents a group which has the same definition as that of $R_{41}$. $R_{59}$ represents a group having the same definition as that of $R_{41}$, an

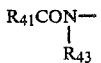

group, an

group, an

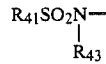

group, an

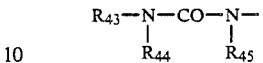

group, an

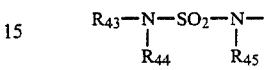

group, an $R_{41}O-$ group, an $R_{41}S-$ group, a halogen atom, or an

group. p represents 0 to 3.

When p is greater than 1, the plural number of $R_{59}$ substituents can be the same or different substituents. Further, each of $R_{59}$ can be a divalent group and bond to form a ring structure. The examples of the divalent groups which may form a ring structure are as follows:

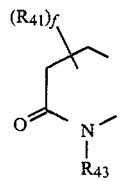

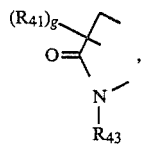

or

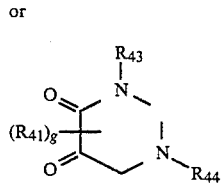

In these formulae, f is an integer of from 0 to 4, g is an integer of from 0 to 2.

$R_{60}$ represents a group having the same definition as that of $R_{41}$. $R_{61}$ represents the group having the same definition as that of $R_{41}$. $R_{62}$ represents a group having the same definition as that of $R_{41}$, an $R_{41}CONH-$ group, an $R_{41}OCONH-$ group, an $R_{41}SO_2NH-$ group, an

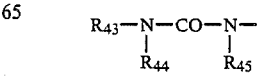

group, an

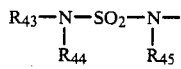

group, an $R_{43}O-$ group, an $R_{41}S-$ group, a halogen atom or an

group. h represents an integer of from 0 to 4. When there are a plural number of $R_{62}$, the $R_{62}$ substituents may be the same or different.

The above-described aliphatic group is a saturated or unsaturated, chain-like or ring-like, linear or branched, and substituted or unsubstituted aliphatic hydrocarbon group having from 1 to 40, preferably from 1 to 22, carbon atoms. Typical examples thereof are a methyl group, an ethyl group, a propyl group, an isopropyl group, a butyl group, a t-butyl group, an i-butyl group, a t-amyl group, a hexyl group, a cyclohexyl group, a 2-ethylhexyl group, an octyl group, a 1,1,3,3-tetramethylbutyl group, a decyl group, a dodecyl group, a hexadecyl group or an octadecyl group.

The aromatic group is a substituted or unsubstituted aromatic group having from 6 to 20 carbon atoms, and preferably is a substituted or unsubstituted phenyl or naphthyl group.

The heterocyclic group is preferably a 3- to 8-membered substituted or unsubstituted heterocyclic group having from 1 to 20, preferably from 1 to 7, carbon atoms, in which at least one hetero atom is a nitrogen atom, an oxygen atom or a sulfur atom. Representative examples of the heterocyclic groups are a 2-pyridyl group, a 4-pyridyl group, a 2-thienyl group, a 2-furyl group, a 2-imidazolyl group, a pyrazinyl group, a 2-pyrimidinyl group, a 1-imidazolyl group, a 1-indolyl group, a phthalimide group, a 1,3,4-thiadiazol-2-yl group, a benzoxazol-2-yl group, a 2-quinolyl group, a 2,4-dioxo-1,3-imidazolidin-5-yl group, a 2,4-dioxo-1,3-imidazolidin-3-yl group, a succinimide group, a phthalimide group, a 1,2,4-triazol-2-yl group, and a 1-pyrazolyl group.

When the above-described aliphatic group, aromatic groups and heterocyclic groups have substituents, representative examples of substituents are a halogen atom, an $R_{47}O-$ group, an $R_{46}S-$ group, an

group, an

group, an

group, an

group, an

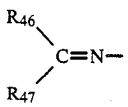

group, an

group, an $R_{46}SO_2-$ group, an $R_{47}OCO-$ group, an

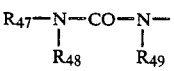

group, an

group, a group having the same definition as that of $R_{46}$, an

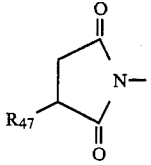

group, an $R_{46}COO-$ group, an $R_{47}OSO_2-$ group, a cyano group, and a nitro group. In this connection, $R_{46}$ represents an aliphatic group, an aromatic group or a heterocyclic group, and $R_{47}$, $R_{48}$ and $R_{49}$ each represents an aliphatic group, an aromatic group, a heterocyclic group or a hydrogen atom. The definitions of the aliphatic group, aromatic group, and heterocyclic group are the same as those described hereinbefore.

The preferred $R_{51}$ through $R_{62}$ and p through h are described hereinafter.

$R_{51}$ is preferably an aliphatic group or an aromatic group. $R_{52}$, $R_{53}$ and $R_{55}$ are preferably an aromatic group. $R_{54}$ is preferably an $R_{41}CONH-$ group or an

group. $R_{56}$ and $R_{57}$ are preferably an aliphatic group, an $R_{41}O-$ group or an $R_{41}S-$ group. $R_{58}$ is preferably an aliphatic group or an aromatic group. In the formula (Cp-6), $R_{59}$ is preferably a chlorine atom, an aliphatic group, or an $R_{41}CONH-$ group; and p is preferably 1 or 2. $R_{60}$ is preferably an aromatic group. In the formula (Cp-7), $R_{59}$ is preferably an $R_{41}CONH-$ group. In the formula (Cp-7), p is preferably 1. $R_{61}$ is preferably an aliphatic group or an aromatic group. In the formula (Cp-8), h is preferably 0 or 1. $R_{62}$ is preferably an $R_{41}O$—CONH— group, an $R_{41}CONH$— group or an $R_{41}SO_2NH$— group and the position of the substituent is preferably in the 5-position on the naphthol ring.

Representative examples of $R_{51}$ through $R_{62}$ are described below.

$R_{51}$ includes a t-butyl group, a 4-methoxyphenyl group, a phenyl group, a 3-[2-(2,4-di-t-amylphenoxy)-butanamido]phenyl group, a 4-octadecyloxyphenyl group, or a methyl group. $R_{52}$ and $R_{53}$ include a 2-chloro-5-dodecyloxycarbonylphenyl group, a 2-chloro-5-hexadecylsulfonamidophenyl group, a 2-chloro-5-tetradecanamidophenyl group, a 2-chloro-5-[4-(2,4-di-t-amylphenoxy)-butanamido]phenyl group, a 2-chloro-5-[2-(2,4-di-t-amylphenoxy)butanamido]phenyl group, a 2-methoxyphenyl group, a 2-methoxy-5-tetradecyloxycarbonylphenyl group, a 2-chloro-5-(1-ethoxycarbonylethoxycarbonyl)phenyl group, a 2-pyridyl group, a 2-chloro-5-octyloxycarbonyl-phenyl group, a 2,4-dichlorophenyl group, a 2-chloro-5-(1-dodecyloxycarbonylethoxycarbonyl)phenyl group, a 2-chlorophenyl group, and a 2-ethoxyphenyl group. $R_{54}$ includes a 3-[2-(2,4-di-t-amylphenoxy)butanamido]-benzamido group, a 3-[4-(2,4-di-t-amylphenoxy)butanamido]-benzamido group, a 2-chloro-5-tetradecanamidoanilino group, a 5-(2,4-di-t-amylphenoxyacetamido)benzamido group, a 2-chloro-5-dodecylsuccinimidoanilino group, a 2-chloro-5-[2-(3-t-butyl-4-hydroxyphenoxy)tetradecanamido]anilino group, a 2,2-dimethylpropanimido group, a 2-(3-pentadecylphenoxy)-butanamido group, a pyrrolidino group, and an N-dibutylamino group. $R_{55}$ preferably includes a 2,4,6-trichlorophenyl group, a 2-chlorophenyl group, a 2,5-dichlorophenyl group, a 2,3-dichlorophenyl group, a 2,6-dichloro-4-methoxyphenyl group, a 4-[2-(2,4-di-t-amylphenoxy)butanamide]phenyl group, and a 2,6-dichloro-4-methanesulfonylphenyl group. $R_{56}$ includes a methyl group, an ethyl group, an isopropyl group, a methoxy group, an ethoxy group, a methylthio group, an ethylthio group, a 3-phenylureido phenoxy)propyl group. $R_{57}$ includes a 3-(2,4-di-t-amylphenoxy)propyl group, a 3-[4-{2-[4-(4-hydroxyphenylsulfonyl)phenoxy]tetradecanamido}-phenyl]propyl group, a methoxy group, an ethoxy group, a methylthio group, an ethylthio group, a methyl group, a 1-methyl-2-{2-octyloxy-5-[2-octyloxy-5-(1,1,3,3-tetramethylbutyl)phenylsulfonamido]phenylsulfonamido}-ethyl group, a 3-[4-(4-dodecyloxyphenylsulfonamido)-phenyl]propyl group, a 1,1-dimethyl-2-[2-octyloxy-5-(1,1,3,3-tetramethylbutyl)phenylsulfonamido]ethyl group, and a dodecylthio group. $R_{58}$ includes a 2-chlorophenyl group, a pentafluorophenyl group, a heptafluoropropyl groupu, a 1-(2,4-di-t-amylphenoxy)propyl group, a 3-(2,4-di-t-amylphenoxy)propyl group, a 2,4-di-t-amylmethyl group, and a furyl group. $R_{59}$ includes a chlorine atom, a methyl group, an ethyl group, a propyl group, a butyl group, an isopropyl group, a 2-(2,4-di-t-amylphenoxy)butanamido group, a 2-(2,4-di-t-amylphenoxy)hexanamido group, a 2-(2,4-di-t-octylphenoxy)octanamido group, a 2-(2-chlorophenoxy)tetradecanamido group, a 2,2-dimethylpropanamido group, a 2-[4-(4-hydroxyphenylsulfonyl)-phenoxy]tetradecanamido group, and a 2-[2-(2,4-di-t-amylphenoxyacetamido)phenoxy]butanamido group. $R_{60}$ includes a 4-cyanophenyl group, a 2-cyanophenyl group, a 4-butylsulfonylphenyl group, a 4-propylsulfonylphenyl group, a 4-ethoxycarbonylphenyl group, a 4-N,N-diethylsulfamoylphenyl group, a 3,4-dichlorophenyl group, and a 3-methoxycarbonylphenyl group. $R_{61}$ includes a dodecyl group, a hexadecyl group, a cyclohexyl group, a butyl group, a 3-(2,4-di-t-amylphenoxy)propyl group, a 4-(2,4-di-t-amylphenoxy)butyl group, a 3-dodecyloxypropyl group, a 2-tetradecyloxyphenyl group, a t-butyl group, a 2-(2-hexyldecyloxy)phenyl group, a 2-methoxy-5-dodecyloxycarbonylphenyl group, a 2-butoxyphenyl group, and a 1-naphthyl group. $R_{62}$ includes an isobutyloxycarbonylamino group, an ethoxycarbonylamino group, a phenylsulfonylamino group, a methanesulfonamido group, a butanesulfonamido group, a 4-methylbenzenesulfonamido group, a benzamido group, a trifluoroacetamido group, a 3-phenylureido group, a butoxycarbonylamino group, and an acetamido group.

$LVG_1$ through $LVG_4$ are explained below.

$LVG_1$ through $LVG_4$ represent a coupling-off group or a hydrogen atom. The preferred examples thereof are described below.

$LVG_1$ is preferably an $R_{65}O$— group, an imido group where a nitrogen atom is bonded at a coupling position (for example, a 2,4-dioxo-1,3-imidazolidin-3-yl group, a 2,4-dioxo-1,3-oxazolidin-3-yl group, a 3,5-dioxo-1,2,4-triazolidin-4-yl group, a succinimido group, a phthalimido group and a 2,4-dioxo-1,3-imidazolidin-1-yl group), an unsaturated nitrogen-containing heterocyclic ring where a nitrogen atom is bonded at a coupling position (for example, a 1-imidazolyl group, a 1-pyrazolyl group, a 1,2,4-triazol-2-(or 4)-yl group, a benzotriazol-1-yl group or a 3-pyrazolin-5-on-2-yl group) and an $R_{66}S$— group.

$LVG_2$ is preferably an $R_{66}S$— group, an unsaturated nitrogen-containing heterocyclic group where a nitrogen atom is bonded at a coupling position (for example, a 1-pyrazolyl group, a 1-imidazolyl group, a 1,2,4-triazol-2(or 4)-yl group, a benzotriazol-1-yl group, or a benzimidazolyl group), an $R_{65}O$— group, or a hydrogen atom.

$LVG_3$ is preferably a halogen atom, an $R_{66}S$— group, an unsaturated nitrogen-containing heterocyclic group where a nitrogen atom is bonded at a coupling position (for example, a 1-pyrazolyl group, a 1-imidazolyl group or a benzotriazol-1-yl group) or a hydrogen atom.

$LVG_4$ is preferably a halogen atom an $R_{66}O$— group, an $R_{66}S$— group, or a hydrogen atom.

$R_{65}$ represents an aromatic group or a heterocyclic group, and $R_{66}$ represents an aliphatic group, an aromatic group or a heterocyclic group. The definitions of the aromatic group, the heterocyclic group and the aliphatic group are the same as those as explained hereinbefore with regard to $R_{41}$.

When $LVG_1$, $LVG_2$ and $LVG_3$ represent the above-described heterocyclic group, they can have substituents. The typical substituents are those as described when $R_{41}$ represents a heterocyclic group.

Representative examples of $LVG_1$, $LVG_2$, $LVG_3$ and $LVG_4$ are described below.

$LVG_1$ includes a 1-benzyl-5-ethoxy-2,4-dioxo-1,3-imidazolidin-3-yl group, a 1-methyl-5-hexyloxy-2,4-dioxo-1,3-imidazolidin-3-yl group, a 1-phenyl-5-benzyl-2,4-dioxo-1,3,5-triazolidin-3-yl group, a 5,5-dimethyl-2,4-dioxo-1,3-oxazolidin-3-yl group, a 1-pyrazolyl group, a 4,5-bis(methoxycarbonyl)imidazol-1-yl group, a 2-phenylcarbamoyl-1,3-imidazol-1-yl group, a 4-phenylcarbamoyl-1,3-imidazol-1-yl group, a 6-methylxanthen-1-yl group, a 4-(4-hydroxyphenylsulfonyl)-phenoxy group, a 4-isopropoxyphenoxy group, a 4- cyanophenoxy group, a 2-chloro-4-(2-chloro-4-hydroxyphenylsulfonyl)phenoxy group, a 5-phenoxycarbonyl-1-benzotriazolyl group, a 4-carboxyphenoxy group, or a 4-(4-benzyloxyphenylsulfonyl)phenoxy group. $LVG_2$ includes a hydrogen atom, a 1-pyrazolyl group, a 3-chloro-5-methyl-1,2,4-triazol-2-yl group, a 5-phenoxycarbonyl-1-benzotriazolyl group, a 2-butoxy-5-(1,1,3,3-tetramethylbutyl)phenylthio group, a 4-chloro-1-pyrazolyl group, a 4-[3-(2-decyl-4-methylphenoxyacetoxy)propyl]pyrazol-1-yl group, a dodecyloxycarbonylmethylthio group, a 1-phenyltetrazolyl-5-thio group, or a 4-dodecylsulfamoylphenoxy group. $LVG_3$ includes a chlorine atom, a hydrogen atom, a 4-methylphenoxy group, a 4-cyanophenoxy group, a 2-butoxy-5-(1,1,3,3-tetramethylbutyl)phenylthio group, a 1-pyrazolyl group, or a 2-(2-phenoxyethoxy)-5-(1,1,3,3-tetramethylbutyl)phenylthio group. $LVG_4$ includes a chlorine atom, a hydrogen atom, a 4-methoxyphenoxy group, a 4-(1,1,3,3-tetramethylbutyl)phenoxy group, a 2-carboxyethylthio group, a 2-(2-carboxyethylthio)ethoxy group, a 1-phenyltetrazolyl-5-thio group, a 1-ethyltetrazolyl-5-thio group, a 3-carboxypropoxy group, a 5-phenoxycarbonylbenzotriazole-1-methoxy group, a 2,3-dihydroxy-4-(1-phenyltetrazolyl-5-thio)-5-propylcarbamoylphenoxy group, a 2-(1-carboxytridecylthio)ethoxy group, a 2-(2-methoxyethylcarbamoyl)ethoxy group, or a 2-[4-(8-acetamido-1-hydroxy-3,6-disulfonaphthyl-2-azo)phenoxy]-ethoxy (disodium salt) group.

The specific examples of couplers which may be used in combination with the present invention are described below. These examples are merely illustrative and are not to be construed as limiting the scope of couplers that may be used with the present invention.

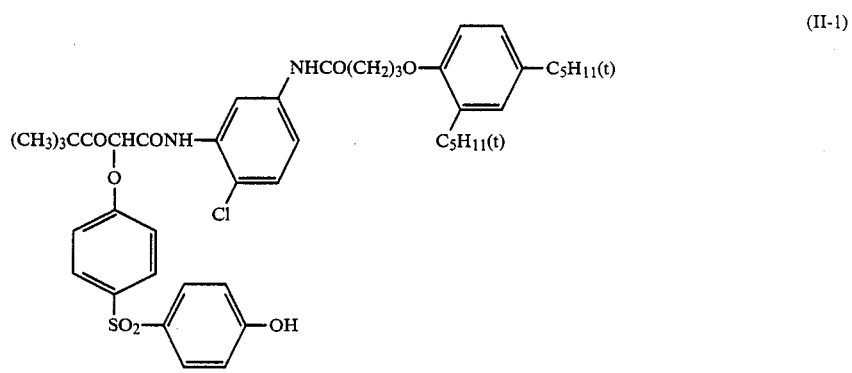

(II-1)

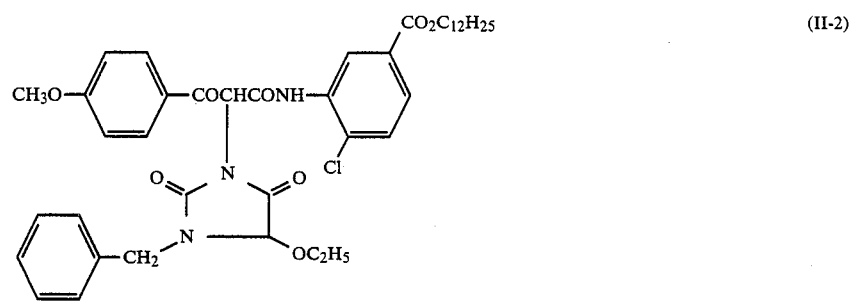

(II-2)

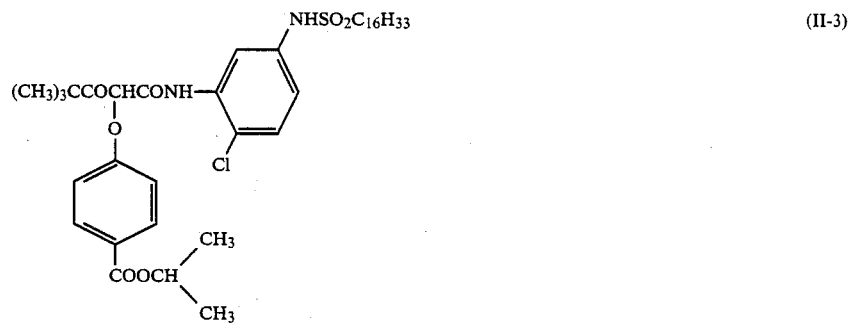

(II-3)

-continued
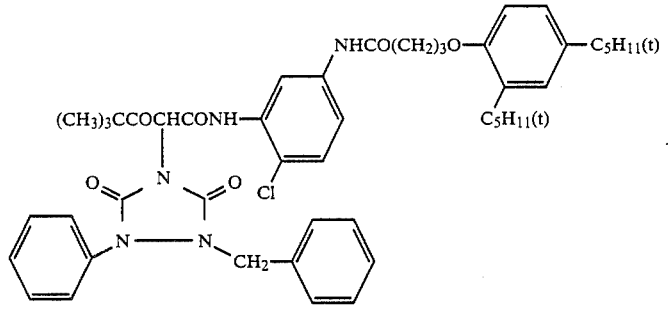
(II-4)
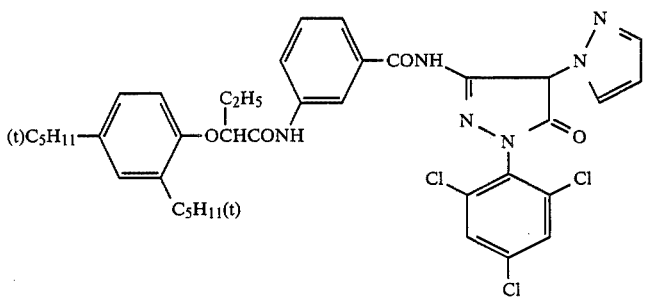
(II-5)
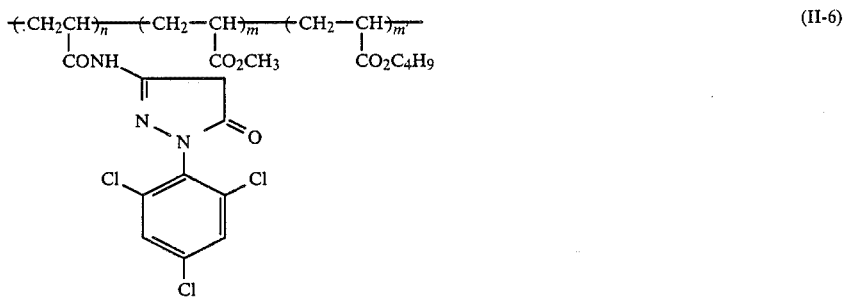
(II-6)
n/m/m' = 2/1/1 (by weight)
average molecular weight: about 4,000
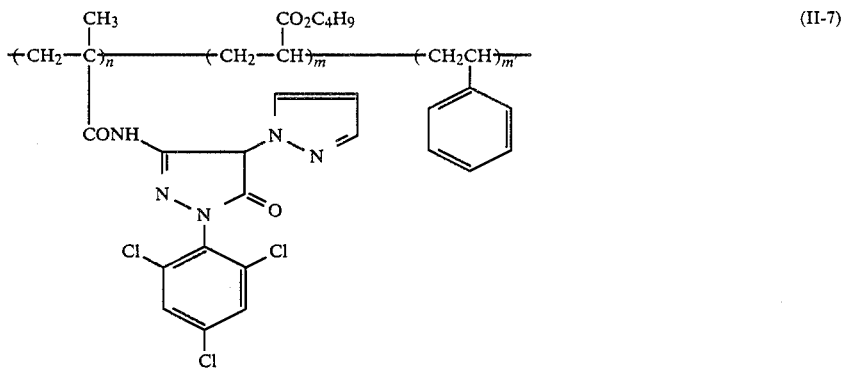
(II-7)
n/m/m' = 50/25/25 (by weight)
average molecular weight: about 20,000
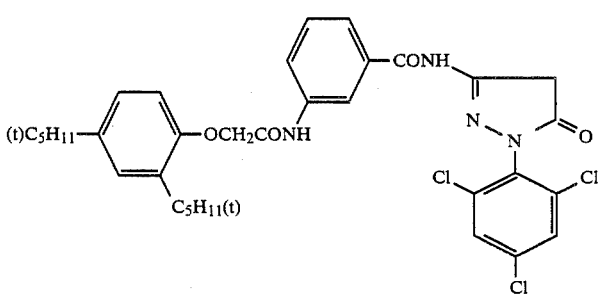
(II-8)

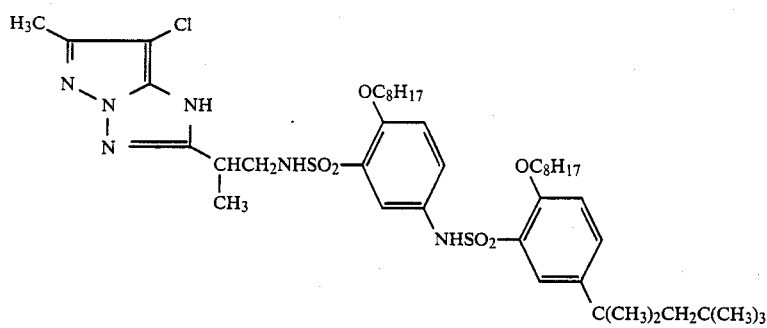
(II-9)
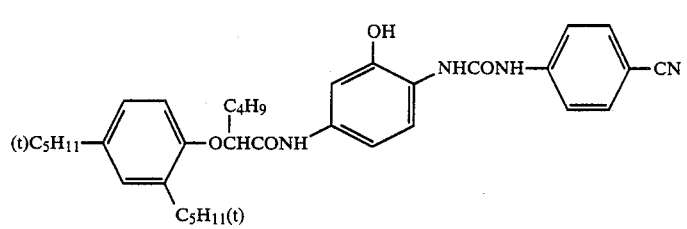
(II-10)
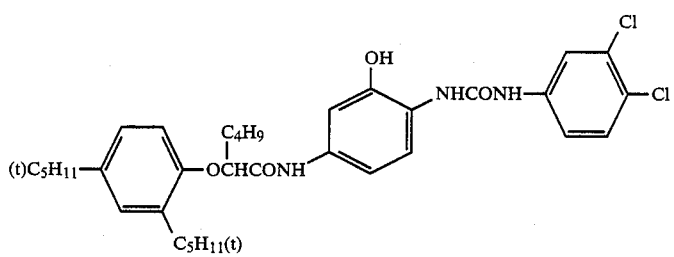
(II-11)
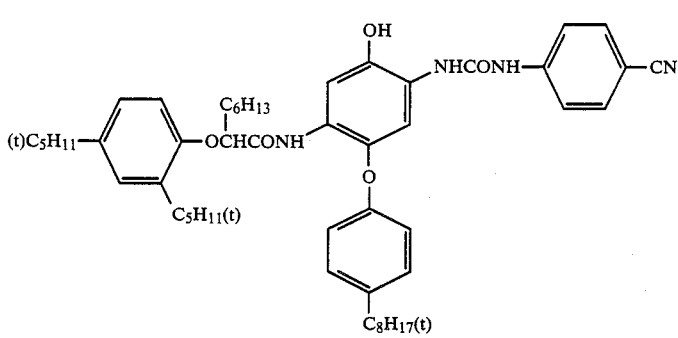
(II-12)
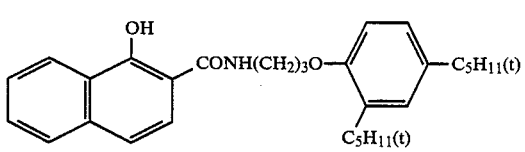
(II-13)
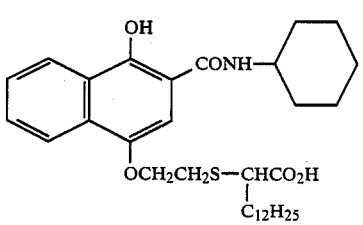
(II-14)

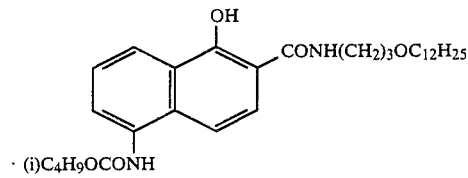 (II-15)

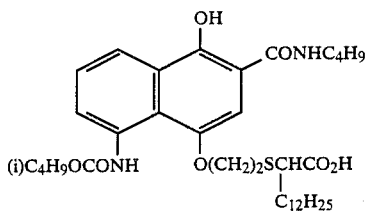 (II-16)

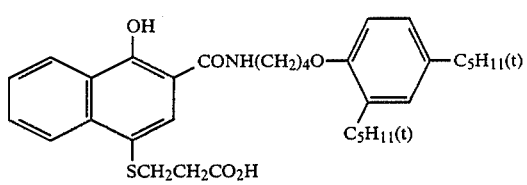 (II-17)

Any silver halide such as silver bromide, silver iodobromide, silver iodochlorobromide, silver chloroiodide or silver chloride can be incorporated into the photographic emulsion layer of the photographic light-sensitive material of the present invention. The preferred silver halide is silver iodobromide or silver iodochlorobromide containing silver iodide in a ratio of about 30 mol% or less. The particularly preferred silver halide is silver iodobromide containing silver iodide in a ratio of from about 2 mol% to about 25 mol%.

Silver halide grains contained in the photographic emulsion can be so-called regular grains having a regular crystal form such as cubic, octahedral, tetradecahedral and so on, spherical grains having an irregular crystal form, grains having crystal defects such as twin crystals or a complex form thereof.

Silver halide grains can be fine grains having grain diameter of about 0.1 micron or lower or can be large grains having projected area diameter of up to about 10 microns. The silver halide emulsion can be a monodispersed emulsion having a narrow grain side distribution or can be a polydispersed emulsion having a wide grain size distribution.

The silver halide photographic emulsion used in the present invention can be prepared in accordance with a known method, for example, a method described in Research Disclosure, RD No. 17643 (December, 1978), pp. 22 and 23, "Emulsion preparation and types", and in Research Disclosure, RD No. 18716 (November, 1979), p. 648.

The photographic emulsion used in the present invention can be prepared in accordance with methods as described in P. Glafkides, Chimie et Physique Photographique, published by Paul Montel (1967), G. F. Duffin, Photographic Emulsion Chemistry, published by Focal Press (1966), and V. L. Zelikman et al., Making and Coating Photographic Emulsions, published by Focal Press (1964). That is, the photographic emulsion of the present invention can be prepared by any method such as an acid method, a neutral method, an ammonia method or the like. The method for reacting water-soluble silver salt with water-soluble halide salt can be a single jet method, a double jet method and the combination thereof. A method for forming grains in an excess amount of silver ion (a so-called "reverse mixing method") can also be employed. As a double jet method, a so-called controlled double jet method where pAg of the solution phase from which silver halide is formed is maintained constant can also be used. In accordance with this method, a silver halide emulsion in which the crystal form is regular and grain size is nearly uniform can be obtained.

Two or more kinds of silver halide emulsions prepared separately beforehand can be mixed and used.

The above-described silver halide emulsions having regular grains can be obtained by controlling pAg and pH while grains are formed. A detailed description thereof is, for example, in Photographic Science and Engineering, Vol. 6, pp. 159 to 165 (1962), Journal of Photographic Science, Vol. 12, pp. 242 to 251 (1964), U.S. Pat. No. 3,655,394 and British Pat. No. 1,413,748.

The typical monodispersed emulsion contains a silver halide grain having an average grain diameter of about 0.1 micron or more and in this emulsion about 95 wt% of the silver grains have a ±40% variation in grain size relative to the average grain diameter. An emulsion of silver halide grains having an average grain diameter of about 0.25 to 2 microns, wherein at least about 95 wt% of the silver grains have ±20% variation in grain size relative to the average grain diameter, can be used in the present invention. The method of preparing such an emulsion is disclosed in U.S. Pat. Nos. 3,574,628 and 3,655,394 and British Pat. No. 1,413,748. The monodispersed emulsion disclosed in Japanese Patent Application (OPI) Nos. 8600/73, 39027/76, 83097/76, 137133/78, 48521/79, 99419/79, 37635/83 and 49938/83 can preferably be used in the present invention.

Tabular grains having an aspect ratio of about 5 or more can also be used in the present invention. Tabular grains can easily be prepared in accordance with methods as disclosed in Gutoff, Photographic Science and Engineering, Vol. 14, pp. 248 to 257 (1970), U.S. Pat. Nos. 4,434,226, 4,414,310, 4,433,048, 4,439,520 and British Pat. No. 2,112,157. It is disclosed in U.S. Pat. No. 4,434,226 that when tabular grains are used, there are advantages such as improved dye sensitizing efficiency by sensitizing dye, improved graininess, and increased sharpness.

Silver halide crystals which have uniform composition, or different halogen composition in the outer portion and inner portion, or has a layered structure can be used in the present invention. The emulsion grains having the above-described characteristics are disclosed in British Pat. No. 1,027,146, U.S. Pat. Nos. 3,505,068 and 4,444,877 and Japanese Patent Application (OPI) No. 143331/85.

Furthermore, crystals of silver halides having different compositions which are bonded by epitaxial junction, and crystals of silver halides and compounds other than silver halides such as silver rhodanide or lead oxide which are bonded can be used. The emulsion grains are disclosed in U.S. Pat. Nos. 4,094,684, 4,142,900, 4,459,353, British Pat. No. 2,038,792, U.S. Pat. Nos. 4,349,622, 4,395,478, 4,433,501, 4,468,087, 3,656,962, 3,852,067 and Japanese Patent Application (OPI) No. 162540/84.

A mixture of the grains having various crystal forms can also be used.

An emulsion which undergoes physical ripening, chemical ripening and spectral sensitization is generally used in the present invention. The additives used during the above-described steps are disclosed in *Research Disclosure*, RD No. 17643 and RD No. 18716, and the locations of the disclosures are listed in the following table.

The known photographic additives used in the present invention are also described in the two *Research Disclosures* cited above, and the locations of the descriptions thereof are also shown in the following table.

| Kinds of Additives | RD No. 17643 | RD No. 18716 |
| --- | --- | --- |
| 1 Chemical Sensitizing Agent | p. 23 | p. 648, right column |
| 2 Sensitivity Increasing Agent | | p. 648, right column |
| 3 Spectral Sensitizing Agent, Supersensitizing Agent | pp. 23 and 24 | p. 648, right column to p. 649, right column |
| 4 Whitening Agent | p. 24 | |
| 5 Antifogging Agent Stabilizer | pp. 24 and 25 | p. 649, right column |
| 6 Light Absorbing Agent, Filter Dye, Ultraviolet Absorbing Agent | pp. 25 and 26 | p. 649, right column to p. 650, left column |
| 7 Stain Preventing Agent | p. 25, right column | p. 650, left to right columns |
| 8 Colored Image Stabilizing Agent | p. 25 | |
| 9 Hardening Agent | p. 26 | p. 651, left column |
| 10 Binder | p. 26 | p. 651, left column |
| 11 Plasticizer, Lubricant | p. 27 | p. 650, right column |
| 12 Coating Aid, Surface Active Agent | pp. 26 and 27 | p. 650, right column |
| 13 Antistatic Agent | p. 27 | p. 650, right column |

"RD" means "Research Disclosure".

The couplers used in the present invention can be introduced into a light-sensitive material by various known dispersing methods. The representative dispersing methods include, for example, a solid dispersing method, an alkaline dispersing method, preferably a latex dispersing method and more preferably an oil-in-water (o/w) dispersing method. The o/w dispersing method comprises dissolving couplers into a single or mixed solution of an organic solvent having a high boiling point such as 175° C. or more and an auxiliary solvent having a low boiling point and then in the presence of a surface active agent finely dispersing couplers in aqueous medium such as water or an aqueous solution of gelatin. Examples of the organic solvent having a high boiling point are disclosed in U.S. Pat. No. 2,322,027 and the like. The dispersing process can be accompanied by phase inversion. The auxiliary solvent is removed or reduced, if necessary, by distillation, noodle washing with water or ultrafiltration and then can be used.

The process and the effect of a latex dispersing method and examples of latex used in an impregnating method are disclosed in U.S. Pat. No. 4,199,363, West German Patent Application (OLS) Nos. 2,541,274 and 2,541,230, and the like.

Suitable supports used in the present invention are disclosed, for example, in the above-described *Research Disclosure*, RD No. 17643, p. 28 and *Research Disclosure*, RD No. 18716, from p. 647, right column to p. 648, left column.

The photographic light-sensitive material prepared in accordance with the present invention is developed by a conventional method as disclosed in the above *Research Disclosure*, RD No. 17643, pp. 28 and 29, and RD No. 18716, p. 651, from the left to the right column.

When a silver halide photographic light-sensitive material of the present invention is a black-and-white light-sensitive material, black-and-white development and fixing are carried out. When it is a color light-sensitive material, color development, bleaching and fixing are conducted and when it is a color reversal light-sensitive material, black-and-white development, reversal, color development, bleaching and fixing are carried out.

The color developing solution used for developing a light-sensitive material of the present invention is an alkaline aqueous solution mainly containing preferably an aromatic primary amine type color developing agent. As a color developing agent, an aminophenol type compound is effective and a p-phenylenediamine type compound is preferably used. The representative examples thereof are 3-methyl-4-amino-N,N-diethylaniline, 3-methyl-4-amino-N-ethyl-N-β-hydroxyethylaniline, 3-methyl-4-amino-N-ethyl-N-β-methanesulfonamidoethylaniline, 3-methyl-4-amino-N-ethyl-N-β-methoxyethylaniline and sulfate, hydrochloride or p-toluenesulfonate thereof. These diamines are preferably used in a form of a salt rather than in a free state, since the salt state is generally more stable.

The color developing solution generally contains pH buffering agents such as carbonates, borates or phosphates of an alkali metal, a development restrainer such as bromide, iodide, benzimidazoles, benzothiazoles, or mercapto compounds or an antifogging agent.

If necessary, preservatives such as hydroxylamine or sulfite, an organic solvent such as triethanolamine or diethylene glycol, a development accelerator such as benzyl alcohol, polyethylene glycol, quaternary ammonium salt, or amines, a dye forming coupler, a competing coupler, a nucleating agent such as sodium boron hydride, an auxiliary developing agent such as 1-phenyl-3-pyrazolidone, a tackifier, a chelating agent such as aminopolycarboxylic acid, aminopolyphosphoric acid, alkyl phosphoric acid, or phosphonocarboxylic acid and antioxidants as disclosed in West German Patent Application (OLS) No. 2,622,950 can be added to the color developing solution.

Regarding the development of the color reversal light-sensitive material, generally a black-and-white development is conducted and then color development is conducted. Conventional black-and-white developing agents such as dihydroxybenzenes (e.g., hydroquinone), 3-pyrazolidones (e.g., 1-phenyl-3-pyrazolidone) or aminophenols (e.g., N-methyl-p-aminophenol) can be used alone or in combination with the black-and-white developing solution.

The photographic emulsion layer after color development is generally bleached. Bleaching step and fixing step may be done simultaneously or separately. To speed up the processing time, bleach-fixing may be done after bleaching. The bleaching agents include, for example, compounds of polyvalent metals such as iron (III), cobalt (III), chromium (VI), or copper (II), peracids, quinones and nitro compounds.

Representative examples of bleaching agents include ferricyanate compounds; dichromate; organic acid complex salts of iron (III) or cobalt (III), in which the organic acids are, for example, aminopolycarboxylic acids such as ethylenediaminetetraacetic acid, diethylenetriaminepentaacetic acid, nitrilotriacetic acid, or 1,3-diamino-2-propanoltetraacetic acid or organic acids such as citric acid, tartaric acid or malic acid; persulfate; manganate; and nitrosophenol and the like. Among these bleaching agents, iron (III) ethylenediaminetetraacetate, iron (III) diethylenetriaminepentaacetate and persulfate are preferred in view of speedy treatment and reduced environmental contamination and pollution. Furthermore, complex salts of iron (III) ethylenediaminetetraacetic acid are particularly effective in a bleaching solution alone or in a monobath bleach-fixing solution.

A bleach accelerating agent can be used in a bleaching solution, bleach-fixing solution and a prebath thereof, if necessary. Specific examples of a bleach accelerating agent are compounds having a mercapto group or a disulfide group, as disclosed in U.S. Pat. No. 3,893,858, West German Pat. Nos. 1,290,812 and 2,059,988, Japanese Patent Application (OPI) Nos. 32736/78, 57831/78, 37418/78, 65732/78, 72623/78, 95630/78, 95631/78, 104232/78, 124424/78, 141623/78 and 28426/78, *Research Disclosure,* RD No. 17129 (July, 1978); thiazolidine derivatives as disclosed in Japanese Patent Application (OPI) No. 140129/75; thiourea derivatives as disclosed in Japanese Patent Publication No. 8506/70, Japanese Patent Application (OPI) Nos. 20832/77 and 32735/78, U.S. Pat. No. 3,706,561; iodide as disclosed in West German Pat. No. 1,127,715 and Japanese Patent Application (OPI) No. 16235/83; polyethylene oxides as disclosed in West German Pat. Nos. 966,410 and 2,748,430; polyamine compounds as disclosed in Japanese Patent Publication No. 8836/70; compounds as disclosed in Japanese Patent Application (OPI) Nos. 42434/74, 59644/74, 94927/78, 35727/79, 26506/80 and 163940/83; iodide ion and bromide ion. Among these compounds, the the compounds as disclosed in U.S. Pat. No. 3,893,858, West German Pat. No. 1,290,812 and Japanese Patent Application (OPI) No. 95630/78 are preferred, since these compounds having a mercapto group or a disulfide group have high accelerating effects. Furthermore, those compounds as disclosed in U.S. Pat. No. 4,552,834 are also preferred. These bleach accelerating agents can be added to a light-sensitive material. These bleach accelerating agents are particularly effective when a color light-sensitive material for photography is bleach-fixed.

The fixing agents include thiosulfate, thiocyanate, thioether compounds, thioureas and iodide used in a large amount. Thilsulfate is most commonly used. The preservatives for a bleach-fixing solution and a fixing solution are preferably a sulfite, a bisulfite or an adduct product of carbonyl bisulfite.

Washing with water and stabilization are generally done after the bleach-fixing or fixing. During the steps of washing with water and stabilization, various known additives can be added to prevent precipitation and to save water. For example, hard water softeners for preventing precipitation such as inorganic phosphoric acid, aminopolycarboxylic acid, organic aminopolyphosphoric acid or organic phosphoric acid, germicides and antifungal agents for preventing the growth of various bacterias, algae and mold, metal salts such as magnesium salt, aluminum salt or bismuth salt, surface active agents for increasing drying load and for preventing drying unevenness, and various hardening agents can be added, if necessary. Furthermore, the compounds as disclosed in L. E. West, *Photographic Science and Engineering,* Vol. 6, pp. 344 through 359 (1965) can also be added. Addition of chelating agents and antifungal agents is particularly effective.

The step of washing with water generally comprises washing with countercurrent water using two or more baths to economize water.

Further, a multistage countercurrent stabilizing treatment as disclosed in Japanese Patent Application No. 8543/82 can be carried out instead of conducting washing with water. In order to conduct washing with water in the present invention, 2 through 9 baths with countercurrent water are necessary. In addition to the above-described additives, various additives can be added to the stabilizing bath to stabilize images. For example, various buffering agents to adjust pH of a film to, for example, pH of 3 through 9 such as borate, metaborate, borax, phosphate, carbonate, potassium hydroxide, sodium hydroxide, aqueous ammonia, monocarboxylic acid, dicarboxylic acid or polycarboxylic acid, which are used in combination and an aldehyde such as formalin can be added. Additionally, various additives such as chelating agents (e.g., inorganic phosporic acid, aminopolycarboxylic acid, organic phosporic acid, organic phosphonic acid, aminopolyphosphonic acid, phosphonocarboxylic acid and so on), germicides (e.g., benzoisothiazolinone, irithiazolone, 4-thiazolinebenzimidazole, halogenated phenol, sulfanilamide, benzotriazole and so on), surface active agents, fluorescent whitening agents or hardening agents can be used and two or more additives having the same or different purposes can be used in combination.

It is preferred that various ammonium salts such as ammonium chloride, ammonium nitrate, ammonium sulfate, ammonium phosphate, ammonium sulfite, or ammonium thiosulfate are added as an agent for adjusting pH of a film.

For the type of color light-sensitive material for photography, the step of washing with water stabilization which is generally conducted after fixation can be replaced by the above-described stabilization step and the washing with water (economizing water) step. In this instance, when a magenta coupler is 2-equivalent, formalin in the stabilizing bath can be removed.

The processing tiem for the washing and stabilization step in the present invention varies depending upon the kinds of light-sensitive materials used and the processing conditions needed and is generally from 20 seconds to 10 minutes, preferably from 20 seconds to 5 minutes.

In order to simplify and to speed up the development process of the silver halide light-sensitive material of the present invention, a color developing agent may be contained in the photographic material itself. It is preferred that precursors of the color developing agents are used in order to be included in the material. For example, indoaniline type compounds as disclosed in U.S. Pat. No. 3,342,597, Schiff base type compounds as disclosed in U.S. Pat. No. 3,342,599 and in *Research Disclosure*, RD Nos. 14850 and 15159, aldol compounds as disclosed in *Research Disclosure*, RD No. 13924, metal salt complexes as disclosed in U.S. Pat. No. 3,719,492, urethane type compounds as disclosed in Japanese Patent Application (OPI) No. 135628/78 and various salt type precursors as disclosed in Japanese Patent Application (OPI) Nos. 6235/81, 16133/81, 59232/81, 67842/81, 83734/81, 83735/81, 83736/81, 89735/81, 81837/81, 54430/81, 106241/81, 107236/81, 97531/82 and 83565/82 are a few examples of preferred agents.

Various types of 1-phenyl-3-pyrazolidones can be included in a silver halide light-sensitive material of the present invention to accelerate color development, if necessary. Typical examples thereof are disclosed in Japanese Patent Application (OPI) Nos. 64339/81, 144547/82, 211147/82, 50532/83, 50536/83, 50533/83, 50534/83, 50535/83, and 115438/83.

The temperature of the various processing solutions used in the present invention is from 10° C. to 50° C. and is generally from 33° C. to 38° C. Raising the temperature shortens processing time, and lowering the temperature improves image quality and stability of the processing solutions.

To save silver in the light-sensitive material of the present invention, cobalt intensification or hydrogen peroxide itensification as disclosed in West German Pat. No. 2,226,770 or in U.S. Pat. No. 3,674,499 can be carried out.

In continuous processing, each processing solution must be replenished to prevent depletion of the ingredients of each solution so that a constant finish can be obtained. The amounts to be replenished can be reduced to half or less than half of the amounts generally used to decrease the cost.

The present invention is illustrated in more detail by the following examples. The examples which follow are illustrative and are not to be construed as limiting the scope of the invention as disclosed herein.

Unless otherwise indicated herein, all parts, percents, ratios and the like are by weight.

EXAMPLE 1

Preparation of Light-Sensitive Silver Halide

Silver iodobromide emulsion (iodide content: 2 mol%) having an average grain diameter of 1.3 μm was prepared from silver nitrate, potassium bromide and potassium iodide by a general ammonia method. Chemical sensitization was carried out by a gold and sulfur sensitizing method using chloroauric acid and sodium thiosulfate. Washing was done by a general precipitation method, and 4-hydroxy-6-methyl-1,3,3a,7-tetraazaindene was added as a stabilizing agent and thus a light-sensitive silver iodobromide emulsion was obtained.

Preparation of Sample Nos. 101 to 113

The emulsion layer containing the thus-prepared light-sensitive silver halide emulsion as above, and the compound represented by formula (I) or the compound for comparison, and the protective layer of an aqueous gelatin solution were uniformly coated on both sides of polyester base having a subbing layer in sequence to prepare Sample Nos. 101 to 113.

The coating amounts on both sides are equal and the total amounts of silver to be coated was 8.0 g/m². The amount of gelatin in the protective layers was 2.6 g/m² and that of the emulsion layers was 5.2 g/m².

Each sample thus prepared was interposed between two fluorescent sensitized papers containing calcium tungstenate, a rectangular wave shape chart made of aluminum was placed in contact with the sample as prepared above as an object to be photographed and X-ray exposure was conducted so that the density became 1.0. Then, each exposed sample was developed with the following developing solution at 35° C. for 25 seconds, fixed, washed with water and dried. Subsequently, MTF (Modulation Transfer Function) of each dried sample was measured by a microphotometer and the results are shown in Table 1.

| Formulation of the Developing Solution: | |
|---|---|
| Potassium Hydroxide | 29.14 g |
| Glacial Acetic Acid | 10.96 g |
| Potassium Sulfite | 44.20 g |
| Sodium Bicarbonate | 7.50 g |
| Boric Acid | 1.00 g |
| Diethylene Glycol | 28.96 g |
| Ethylenediaminetetraacetic Acid | 1.67 g |
| 5-Methylbenzotriazole | 0.06 g |
| 5-Nitroindazole | 0.25 g |
| Hydroquinone | 30.00 g |
| 1-Phenyl-3-pyrazolidone | 1.50 g |
| Glutaraldehyde | 4.93 g |
| Sodium Metabisulfite | 12.60 g |
| Water to make | 1 liter |

TABLE 1

| Sample No. | Compound (I) Structure | Amount Added (mol/mol Ag) | MTF 0.5 line/mm | MTF 1.0 line/mm | Remarks |
|---|---|---|---|---|---|
| 101 | — | — | 0.81 | 0.62 | Control |
| 102 | (I-1) | $5 \times 10^{-3}$ | 0.85 | 0.69 | Invention |
| 103 | (I-1) | $10 \times 10^{-3}$ | 0.89 | 0.72 | " |
| 104 | (I-2) | $5 \times 10^{-3}$ | 0.86 | 0.69 | " |
| 105 | (I-2) | $10 \times 10^{-3}$ | 0.90 | 0.74 | " |
| 106 | (I-8) | $5 \times 10^{-3}$ | 0.84 | 0.68 | " |
| 107 | (I-8) | $10 \times 10^{-3}$ | 0.88 | 0.72 | " |
| 108 | (I-22) | $5 \times 10^{-3}$ | 0.85 | 0.68 | " |
| 109 | (I-22) | $10 \times 10^{-3}$ | 0.88 | 0.72 | " |
| 110 | (B) | $5 \times 10^{-3}$ | 0.82 | 0.63 | Comparison |
| 111 | (B) | $10 \times 10^{-3}$ | 0.83 | 0.65 | " |

TABLE 1-continued

| Sample No. | Compound (I) Structure | Amount Added (mol/mol Ag) | MTF 0.5 line/mm | 1.0 line/mm | Remarks |
|---|---|---|---|---|---|
| 112 | (C) | $5 \times 10^{-3}$ | 0.83 | 0.66 | " |
| 113 | (C) | $10 \times 10^{-3}$ | 0.84 | 0.68 | " |

Compound (B) for Comparison: (compound as disclosed in U.S. Pat. No. 4,476,219)

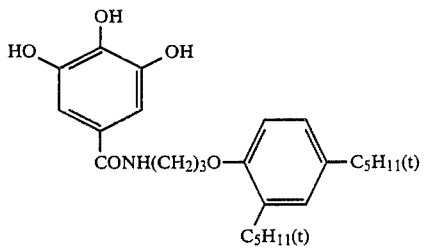

Compound (C) for Comparison: (compound as disclosed in British Pat. No. 1,400,149)

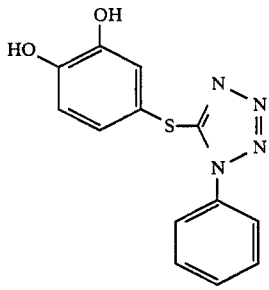

As is clear from the results in Table 1, the photographic materials containing the compounds of the present invention exhibit larger MTF values and better sharpness than those of the comparative samples containing no compounds of the present invention, particularly the comparative samples containing Compounds (B) and (C).

EXAMPLE 2

A multilayered color light-sensitive material was prepared by providing on a polyethylene terephthalate film support multiple layers having the following composition.
First Layer: Antihalation Layer
  A gelatin layer containing black colloidal silver.
Second Layer: Intermediate Layer
  A gelatin layer containing an emulsified dispersion of 2,5-di-t-octylhydroquinone.
Third Layer: First Red-Sensitive Emulsion Layer
  Silver iodobromide emulsion (silver iodide: 5 mol%)

| | Amount of silver coated 1.6 g/m² |
|---|---|
| Sensitizing Dye I | $4.5 \times 10^{-4}$ mol/mol Ag |
| Sensitizing Dye II | $1.5 \times 10^{-4}$ mol/mol Ag |
| Coupler EX-1 | 0.03 mol/mol Ag |
| Coupler EX-3 | 0.003 mol/mol Ag |

Fourth Layer: Second Red-Sensitive Emulsion Layer
  Silver iodobromide emulsion (silver iodide: 10 mol%)

| | Amount of silver coated 1.4 g/m² |
|---|---|
| Sensitizing Dye I | $3 \times 10^{-4}$ mol/mol Ag |
| Sensitizing Dye II | $1 \times 10^{-4}$ mol/mol Ag |
| Coupler EX-1 | 0.002 mol/mol Ag |
| Coupler EX-2 | 0.02 mol/mol Ag |
| Coupler EX-3 | 0.0016 mol/mol Ag |

Fifth Layer: Intermediate Layer
  The same as the second layer.
Sixth Layer: First Green-Sensitive Emulsion Layer
  Silver iodobromide emulsion (silver iodide: 6 mol%)

| | Amount of silver coated 1.5 g/m² |
|---|---|
| Sensitizing Dye III | $5 \times 10^{-4}$ mol/mol Ag |
| Sensitizing Dye IV | $2 \times 10^{-4}$ mol/mol Ag |
| Coupler EX-4 | 0.05 mol/mol Ag |
| Coupler EX-5 | 0.008 mol/mol Ag |
| Compound EX-10 | 0.0015 mol/mol Ag |

Seventh Layer: Second Green-Sensitive Emulsion Layer
  Silver iodobromide emulsion (silver iodide: 8 mol%)

| | Amount of silver coated 1.3 g/m² |
|---|---|
| Sensitizing Dye III | $3 \times 10^{-4}$ mol/mol Ag |
| Sensitizing Dye IV | $1.2 \times 10^{-4}$ mol/mol Ag |
| Coupler EX-7 | 0.017 mol/mol Ag |
| Coupler EX-6 | 0.003 mol/mol Ag |

Eighth Layer: Yellow Filter Layer
  A gelatin layer containing an emulsified dispersion of yellow colloidal silver and 2,5-di-t-octylhydroquinone in an aqueous gelatin solution.
Ninth Layer: First Blue-Sensitive Emulsion Layer
  Silver iodobromide emulsion (silver iodide: 6 mol%)

| | Amount of silver coated 0.7 g/m² |
|---|---|
| Coupler EX-8 | 0.25 mol/mol Ag |
| Coupler EX-9 | 0.015 mol/mol Ag |

Tenth Layer: Second Blue-Sensitive Emulsion Layer
  Silver iodobromide emulsion (silver iodide: 6 mol%)

| | Amount of silver coated 0.6 g/m² |
|---|---|
| Coupler EX-8 | 0.06 mol/mol Ag |

Eleventh Layer: First Protective Layer
  Silver iodobromide emulsion (silver iodide 1 mol%, average grain diameter 0.07 μm)
    Amount of silver coated 0.5 g/m²
  A gelatin layer containing an emulsified dispersion of Ultraviolet Absorbing Agent UV-1

Twelfth Layer: Second Protective Layer

A gelatin layer containing particles of polymethyl methacrylate (diameter: about 1.5 μm)

Gelatin Hardening Agent H-1 and a surface active agent were added to each of the above layers in addition to the above-described composition. Thus, the prepared sample was identified as Sample No. 201.

Preparation of Sample Nos. 202 through 209

The same procedure as in the preparation of Sample No. 201 was repeated except that Compound EX-10 used in the green-sensitive emulsion layer of Sample No. 201 was changed to those compounds shown in Table 2.

Sample Nos. 201 to 209 were exposed through a wedge to white light and processed in the manner as hereinafter referred to and all samples had nearly the same sensitivities and same gradation.

The chemical formulae of the compounds used herein are illustrated as follows.

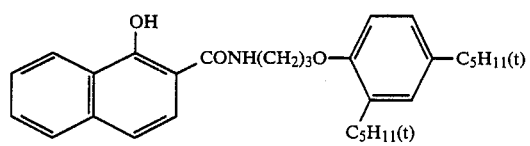

Coupler EX-1

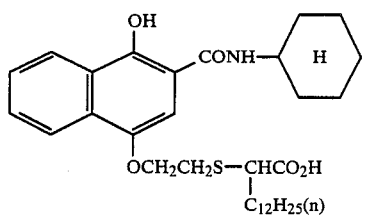

Coupler EX-2

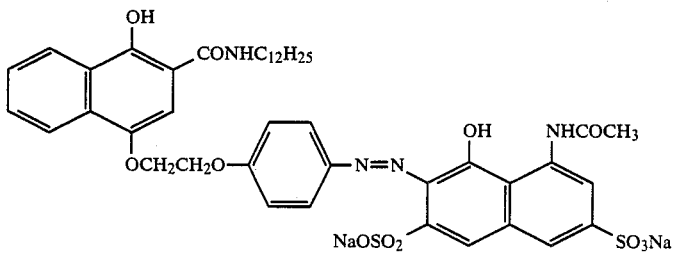

Coupler EX-3

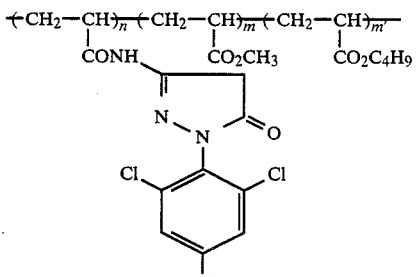

Coupler EX-4 n/m/m' = 2/1/1 (by weight)
average molecular weight: about 4,000

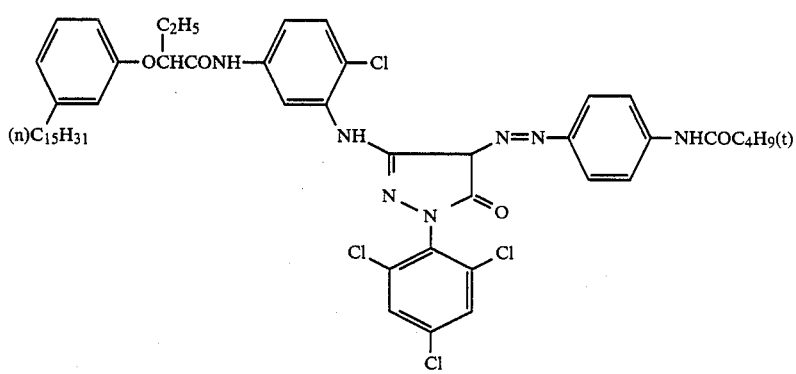

Coupler EX-5

-continued
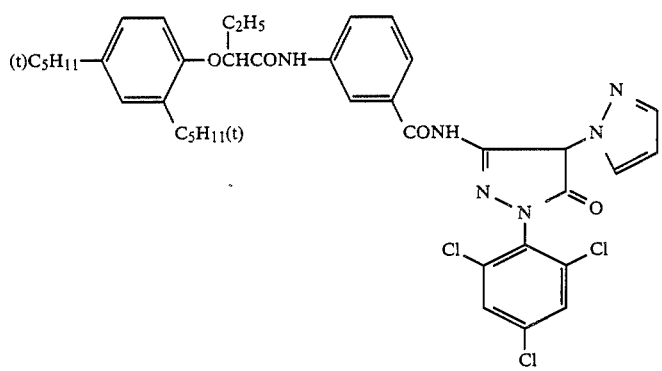
Coupler EX-6
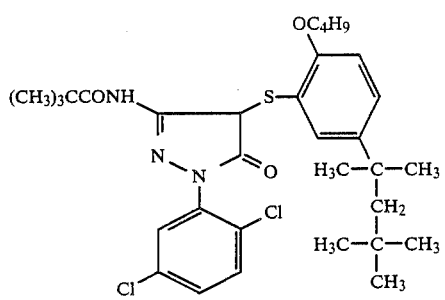
Coupler EX-7
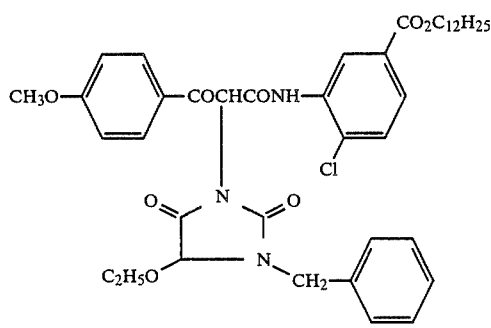
Coupler EX-8
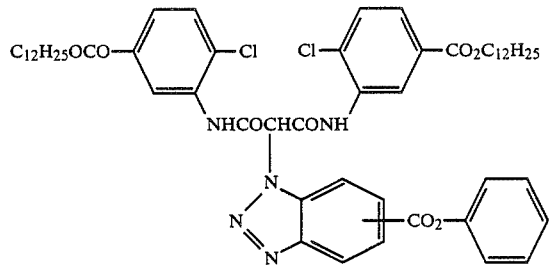
Coupler EX-9
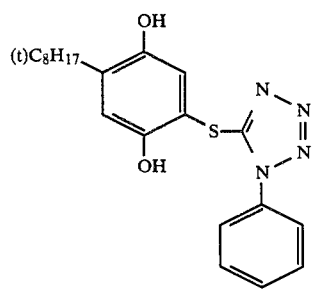
EX-10
(compound described in U.S. Pat. No. 3,930,863)

-continued
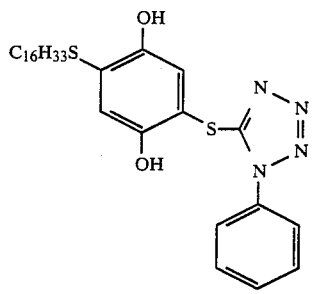
(compound described in U.S. Pat. No. 4,144,071)
EX-11
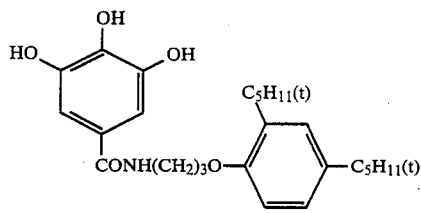
(compound described in U.S. Pat. No. 4,476,219)
EX-12
$(CH_2=CH-SO_2CH_2CONHCH_2)_2$   H-1
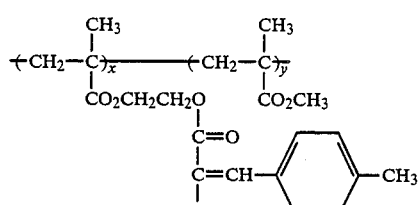
x/y = 7/3 (by weight)
UV-1
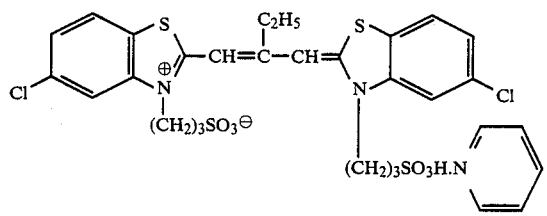
Sensitizing Dye I
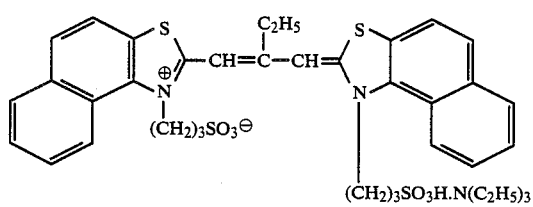
Sensitizing Dye II
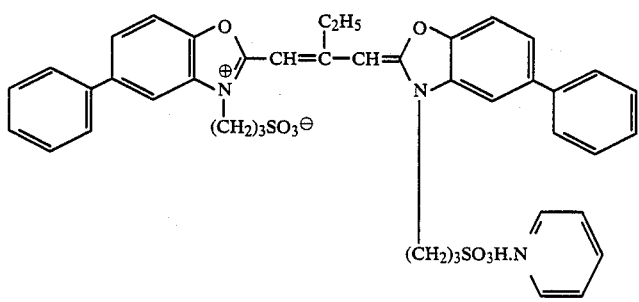
Sensitizing Dye III -continued

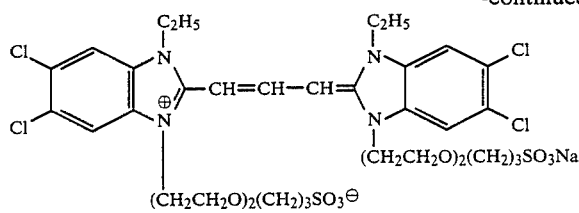

Sensitizing Dye IV

Development was conducted at 38° C. in the following manner.

| Color Development | 3 min 15 sec |
|---|---|
| Bleaching | 6 min 30 sec |
| Washing with Water | 2 min 10 sec |
| Fixing | 4 min 20 sec |
| Washing with Water | 3 min 15 sec |
| Stabilization | 1 min 05 sec |

The composition of the processing solutions used in each step was as follows.

| Color Developing Solution: | |
|---|---|
| Diethylenetriaminepentaacetic Acid | 1.0 g |
| 1-Hydroxyethylidene-1,1-diphosphonic Acid | 2.0 g |
| Sodium Sulfite | 4.0 g |
| Potassium Carbonate | 30.0 g |
| Potassium Bromide | 1.4 g |
| Potassium Iodide | 1.3 mg |
| Hydroxylamine Sulfate | 2.4 g |
| 4-(N—Ethyl-N—β-hydroxyethylamino)-2-methylaniline Sulfate | 4.5 g |
| Water to make | 1 liter |
| | pH 10.0 |
| Bleaching Solution: | |
| Fe (III) Ammonium Ethylenediaminetetraacetate | 100.0 g |
| Disodium Ethylenediaminetetraacetate | 10.0 g |
| Ammonium Bromide | 150.0 g |
| Ammonium Nitrate | 10.0 g |
| Water to make | 1 liter |
| | pH 6.0 |
| Fixing Solution: | |
| Disodium Ethylenediaminetetraacetate | 1.0 g |
| Sodium Sulfite | 4.0 g |
| Aqueous Solution of Ammonium Thiosulfate (70%) | 175.0 ml |
| Sodium Bisulfite | 4.6 g |
| Water to make | 1 liter |
| | pH 6.6 |
| Stabilizing Solution: | |
| Formalin (40%) | 2.0 ml |
| Polyoxyethylene-p-mononylphenylether (average degree of polymerization: 10) | 0.3 g |
| Water to make | 1.0 liter |

Graininess of magenta color images of these samples was measured by a conventional RMS (Root Mean Square) method. Evaluation of graininess by RMS method is known to those skilled in this industry and is disclosed in *Photographic Science and Engineering,* Vol. 19, No. 4 (1975), pp. 235 to 238, in an article entitled "RMS Granularity: Determination of just noticeable difference".

Values obtained by the RMS method at a density of 0.3 are shown in Table 2.

TABLE 2

| Sample No. | Compounds Added in First Green-Sensitive Layer* | Amount Added** | RMS Value |
|---|---|---|---|
| 201 (Comparison) | EX-10 | 1.0 | 0.0168 |

TABLE 2-continued

| Sample No. | Compounds Added in First Green-Sensitive Layer* | Amount Added** | RMS Value |
|---|---|---|---|
| 202 (Comparison) | EX-11 | 1.0 | 0.0165 |
| 203 (Comparison) | EX-12 | 3.0 | 0.0163 |
| 204 (Invention) | (I-1) | 1.0 | 0.0158 |
| 205 (Invention) | (I-3) | 2.0 | 0.0158 |
| 206 (Invention) | (I-5) | 1.0 | 0.0158 |
| 207 (Invention) | (I-7) | 2.5 | 0.0160 |
| 208 (Invention) | (I-10) | 1.5 | 0.0158 |
| 209 (Invention) | (I-15) | 1.5 | 0.0157 |

*These compounds were added to the first green-sensitive layer instead of Compound EX-10.
**The amount is shown in terms of a relative mol value when the number of mol of the additive amount of EX-10 is assumed to be 1.

As can be seen from Table 2, samples containing compounds of the present invention have RMS values which are lower than the RMS values obtained with the prior art materials, and are accordingly excellent in graininess.

EXAMPLE 3

A sample of a multilayered color light-sensitive material was prepared by providing layers having the following formulation on a polyethylene terephthalate film support.

First Layer: Antihalation Layer
Gelatin layer containing black colloidal silver.

Second Layer: Intermediate Layer
Gelatin layer containing an emulsified dispersion of 2,5-di-t-octylhydroquinone.

Third Layer: Red-Sensitive Emulsion Layer
Silver iodobromide emulsion (silver iodide: 7 mol%)

| | Amount of silver coated 2.0 g/m² |
|---|---|
| Sensitizing Dye I | 4.5 × 10⁻⁴ mol/mol Ag |
| Sensitizing Dye II | 1.5 × 10⁻⁴ mol/mol Ag |
| Coupler EX-1 | 0.04 mol/mol Ag |
| Coupler EX-3 | 0.003 mol/mol Ag |
| Compound EX-10 | 0.004 mol/mol Ag |
| Tricresyl Phosphate | 0.5 g/m² |
| Dibutyl Phthalate | 0.2 g/m² |

Fourth Layer: First Protective Layer
Silver iodobromide (silver iodide: 1 mol%, average grain diameter: 0.07 μm)
Amount of silver coated 0.5 g/m²
A gelatin layer containing an emulsified dispersion of Ultraviolet Absorbing Agent UV-1.

Fifth Layer: Second Protective Layer
A gelatin layer containing particles of polymethyl methacrylate (diameter: about 1.5 μm).

Gelatin Hardening Agent H-1 and a surface active agent were added to each of the above layers in addition to the above-described composition. The thus-prepared sample was identified as Sample No. 301.

Preparation of Sample Nos. 302 to 309

The same procedure as in the preparation of Sample No. 301 was repeated except that Compound EX-10 used in Sample No. 301 was changed to those compounds as shown in Table 3 provided that the amount is the same.

The compound used to prepare samples:

EX-13 (compound included in British Patent 1,400,149)

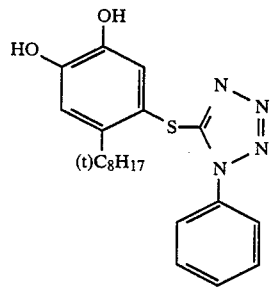

The same compounds as those used in Example 2 were used except EX-13 and those of the present invention.

The samples of No. 301 through No. 309 were allowed to stand at room temperature or at 45° C. and at 80% RH for 3 days to evaluate storage stability of the test films. Then these samples were exposed through a wedge to white light, and subjected to the following processing and sensitometry. The results are shown in Table 3.

The following processing was performed at 20° C.

| 1. Development | 10 min |
|---|---|
| 2. Stopping | 1 min |
| 3. Fixing | 5 min |
| 4. Washing with Water | 10 min |

The processing solutions of each step are as follows.

| Development: | |
|---|---|
| Sodium Sulfite | 33 g |
| Metol (N—methyl-p-aminophenol.½sulfate) | 3 g |
| Hydroquinone | 3 g |
| Sodium Carbonate (monohydrate) | 23 g |
| Potassium Bromide | 1.7 g |
| $H_2O$ | 1 liter |
| Stopping: | |
| Glacial Acetic Acid | 15 ml |
| $H_2O$ | 1 liter |
| Fixing: | |
| Sodium Thiosulfate | 191 g |
| Sodium Sulfite | 20 g |
| Glacial Acetic Acid | 20 ml |
| $H_2O$ | 1 liter |

TABLE 3

| Sample No. | Compound | Relative Sensitivity* (%) |
|---|---|---|
| 301 (Comparison) | EX-10 | 78 |
| 302 (Comparison) | EX-11 | 89 |
| 303 (Comparison) | EX-13 | 80 |
| 304 (Invention) | (I-1) | 98 |
| 305 (Invention) | (I-3) | 98 |
| 306 (Invention) | (I-4) | 98 |

TABLE 3-continued

| Sample No. | Compound | Relative Sensitivity* (%) |
|---|---|---|
| 307 (Invention) | (I-5) | 98 |
| 308 (Invention) | (I-8) | 97 |
| 309 (Invention) | (I-18) | 97 |

*Relative sensitivity is the sensitivity of samples which were allowed to stand at 45° C. and 80% RH for 3 days divided by the sensitivity of samples which were allowed to stand at room temperature for 3 days times 100.

It is clear from the results in Table 3 that the compound of the present invention is excellent in stability with passage of time. On the other hand, it is believed that the compound for comparison was decomposed by oxidation with air, and the development restrainer was cleaved during the storage, resulting in decreasing sensitivity.

While the invention has been described in detail and with reference to specific embodiments thereof, it will be apparent to one skilled in the art that various changes and modifications can be made therein without departing from the spirit and scope thereof.

What is claimed is:

1. A silver halide photographic material comprising a support having provided thereon at least one light-sensitive silver halide emulsion layer, said silver halide emulsion layer or a layer adjacent to said emulsion layer comprising a compound represented by the following formula (I):

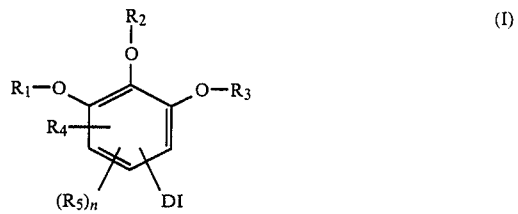

wherein $R_1$, $R_2$ and $R_3$, which may be the same or different, each represents a hydrogen atom or a group cleaved by an alkali; $R_4$ represents an electron attracting group having $\sigma p$ value of Hammett's substituent constant of 0.3 or more; $R_5$ represents a group substitutable on the benzene ring; n represents 0 to 1; and DI represents a development restrainer or a precursor thereof; and when any two of $R_1$, $R_2$, $R_3$, $R_4$, and $R_5$ are adjacent each other, each of said two groups may represent a divalent group and said two groups may be bonded to form a heterocyclic group.

2. The silver halide photographic material as claimed in claim 1, wherein $R_1$, $R_2$, and $R_3$ each is a hydrogen atom.

3. The silver halide photographic material as claimed in claim 1, wherein said group cleaved by alkali is an $R_6$—CO— group, an $R_6$OCO— group, an $NCCH_2CH_2$— group or an $R_6SO_2CH_2Ch_2$— group, in which $R_6$ represents an aliphatic group, an aromatic group or a heterocyclic group.

4. The silver halide photographic material as claimed in claim 1, wherein when $R_1$ and $R_2$ combine to form a ring structure, said compound is represented by the following formulae:

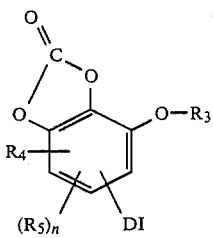

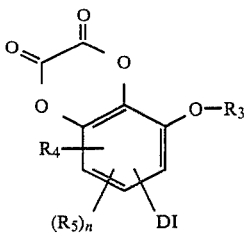

wherein R₃, R₄, and R₅ are the same as defined in claim 1.

5. The silver halide photographic material as claimed in claim 1, wherein R₄ is an R₉OOC— group, an R₉NR₁₀CO— group, an R₇SO₂ group, an R₉NR₁₀SO₂— group, an R₉CO— group, or a cyano group in which R₇ represents an aliphatic group, an aromatic group, or a heterocyclic group; and R₉ and R₁₀ each represents a hydrogen atom, an aliphatic group, an aromatic group, or a heterocyclic group.

6. The silver halide photographic material as claimed in claim 1, wherein n is 0.

7. The silver halide photographic material as claimed in claim 1, wherein R₅ is a halogen atom, an R₈— group, or an R₈S— group in which R₈ represents an aliphatic group, an aromatic group, or a heterocyclic group.

8. The silver halide photographic material as claimed in claim 5, wherein said aliphatic group is a saturated or unsaturated, chain-like or ring-like, linear or branched, substituted or unsubstituted group having from 1 to 40 carbon atoms;
said aromatic group is a substituted or unsubstituted phenyl or naphthyl group having from 6 to 20 carbon atoms; and
said heterocyclic group is a 3- to 8-membered ring containing one or more hetero atoms selected from the group consisting of one or more nitrogen atoms, one or more oxygen atoms, or one or more sulfur atoms, and from 1 to 7 carbon atoms.

9. The silver halide photographic material as claimed in claim 1, wherein DI is a development restrainer selected from the group consisting of a tetrazolylthio group, a thiazolylthio group, a benzothiazolylthio group, a benzoxazolylthio group, a benzotriazolyl group, an indazolyl group, a benzimidazolylthio group, a triazolylthio group, a thiadiazolylthio group, a thioether-substituted triazolyl group, and an oxadiazolylthio group.

10. The silver halide photographic material as claimed in claim 1, wherein DI represents a development restrainer precursor of the formula:

\*—TIME—DI' wherein \* represents the position at which a group except DI is bonded in formula (I) in claim 1, TIME represents a group which cleaves DI' after being cleaved as TIME—DI', and DI' is a development restrainer selected from the group consisting of a tetrazolylthio group, a thiazolylthio group, a benzothiazolylthio group, a benzoxazolylthio group, a benzotriazolyl group, an indazolyl group, a benzimidazolylthio group, a triazolylthio group, a thiadiazolylthio group, a thioether-substituted triazolyl group, and an oxadiazolylthio group.

11. The silver halide photographic material as claimed in claim 1, wherein said photographic material is a multilayer, multicolor photographic material comprising multiple layers having at least two different spectral sensitivities.

12. The silver halide photographic material as claimed in claim 11, wherein said compound is incorporated into the photographic material in an amount of from $1 \times 10^{-7}$ to 0.5 mol per mol of silver which is present in the same layer as said compound or in a layer which is adjacent to the layer containing said compound.

13. The silver halide photographic marterial as claimed in claim 12, wherein said compound is incorporated into the photographic material in an amount of from $1 \times 10^{-6}$ to $1 \times 10^{-1}$ mol per mol of silver which is present in the same layer as said compound or in a layer which is adjacent to the layer containing said compound.

14. The silver halide photographic material as claimed in claim 11, wherein photographic material further comprises a coupler together with said compound of formula (I) in the same layer.

15. The silver halide photographic material as claimed in claim 14, wherein the weight ratio of said compound to said coupler is 1/99 to 50/50 by mol.

16. The silver halide photographic material as claimed in claim 1, wherein said photographic material is a silver halide photographic material for a photomechanical process which has a silver chlorobromide or silver chloroiodobromide emulsion layer containing at least 60 mol% silver chloride and 0 to 5 mol% silver iodide relative to the total silver halide concentration and which has polyalkylene oxides.

17. The silver halide photographic material as claimed in claim 16, wherein said compound is incorporated into the photographic material in an amount of from $1 \times 10^{-7}$ to $1 \times 10^{-1}$ mol per mol of silver halide.

18. The silver halide photographic material as claimed in claim 17, wherein said compound is incorporated into the photographic material in an amount of from $1 \times 10^{-6}$ to $1 \times 10^{-2}$ mol per mol of silver halide.

19. The silver halide photographic material as claimed in claim 1, wherein said photographic material has a monodispersed silver halide emulsion layer which is capable of forming a superhigh contrast negative image with a stable developing solution in the presence of hydrazine derivatives.

20. The silver halide photographic material as claimed in claim 19, wherein said compound is incorporated into the photographic material in an amount of from $1 \times 10^{-5}$ to $8 \times 10^{-2}$ mol per mol of silver halide.

21. The silver halide photographic material as claimed in claim 20, wherein said compound is incorporated into the photographic material in an amount of from $1 \times 10^{-4}$ to $5 \times 10^{-2}$ mol per mol of silver halide.

22. The silver halide photographic material as claimed in claim 1, wherein said photographic material is a black-and-white photographic material having on at least one of the surfaces of the support a silver iodobromide or silver chloroiodobromide emulsion layer containing silver chloride of from 0 to 50 mol% and silver iodide of not more than 15 mol%.

23. The silver halide photographic material as claimed in claim 22, wherein said black-and-white photographic material is a light-sensitive material for X-ray photography.

24. The silver halide photographic material as claimed in claim 22, wherein said compound is incorporated into the photographic material in an amount of from $1\times10^{-6}$ to $1\times10^{-1}$ mol per mol of silver halide.

25. The silver halide photographic material as claimed in claim 24, wherein said compound is incorporated into the photographic material in an amount of from $1\times10^{-5}$ to $5\times10^{-2}$ mol per mol of silver halide.

* * * * *